United States Patent
Gouliaev et al.

(10) Patent No.: US 7,208,527 B2
(45) Date of Patent: Apr. 24, 2007

(54) POTASSIUM CHANNEL MODULATORS

(75) Inventors: Alex Haahr Gouliaev, Vekso (DK); Frank Abildgaard Slok, Copenhagen (DK); Lene Teuber, Vaerlose (DK); Joachim Demnitz, Copenhagen (DK)

(73) Assignee: Poseidon Pharmaceuticals A/S, Ballerup (DK)

( * ) Notice: Subject to any disclaimer, the term of this patent is extended or adjusted under 35 U.S.C. 154(b) by 283 days.

(21) Appl. No.: 10/496,859

(22) PCT Filed: Jan. 6, 2003

(86) PCT No.: PCT/DK03/00004

§ 371 (c)(1), (2), (4) Date: Jul. 13, 2004

(87) PCT Pub. No.: WO03/059873

PCT Pub. Date: Jul. 24, 2003

(65) Prior Publication Data

US 2005/0009816 A1    Jan. 13, 2005

(30) Foreign Application Priority Data

Jan. 4, 2002  (DK) ............................. 2002 00013

(51) Int. Cl.
*A61K 31/16* (2006.01)
*C07C 233/00* (2006.01)

(52) U.S. Cl. ...................... 514/613; 564/123
(58) Field of Classification Search ................ 564/123; 514/613
See application file for complete search history.

(56) References Cited

U.S. PATENT DOCUMENTS 3,818,030 A    6/1974   Timmler et al.
5,070,087 A   12/1991   Teng et al.

FOREIGN PATENT DOCUMENTS

| WO | WO 97/34589 A1 | 9/1997 |
|---|---|---|
| WO | WO 97/34599 A2 | 9/1997 |
| WO | WO 00/06137 A2 | 2/2000 |
| WO | WO 00/50026 A1 | 8/2000 |
| WO | WO 00/69439 A1 | 11/2000 |
| WO | WO 01/27070 A1 | 4/2001 |
| WO | WO 01/30327 A2 | 5/2001 |
| WO | WO 01/49663 A2 | 7/2001 |
| WO | WO-2005/061463 A1 | 7/2005 |
| WO | WO-2006/136837 A2 | 12/2006 |

OTHER PUBLICATIONS

Kigasawa, et al (Japanese Pat. No. 49-1544, issued Jan. 8, 1974).*
Sundberg, et al (J. Org. Chem., vol. 34, No. 9, pp. 2799-2801, 1969).*
Marchand, et al (Tetrahedron, vol. 30, Iss. 17, pp. 3185-3192, 1974).*
Wu et al., Journal of Polymer Science, Part A., Polymer Chemistry, vol. 36, No. 12, pp. 2013-2019 (1998).
Williams et al., Tetrahedron Letters, vol. 32, No. 52, pp. 7633-7636 (1991).
Maharajh et al., Can. J. Chem., vol. 75, pp. 140-161 (1997).
Kessel et al., Biochemical Pharmacology, vol. 25, pp. 1893-1897 (1976).
Shi et al., Bull. Chem. Soc., vol. 63, pp. 453-460 (1990).
Dhar et al., J. Med. Chem., vol. 37, pp. 2334-2342 (1994).
Grochowski et al., Novel synthesis of N-alkylated lactams, Heterocycles, (1976), vol. 5, pp. 101-108.

* cited by examiner

*Primary Examiner*—Kamal A. Saeed
*Assistant Examiner*—Susannah L. Chung
(74) *Attorney, Agent, or Firm*—Birch, Stewart, Kolasch & Birch, LLP

(57) ABSTRACT

This invention relates to novel compounds useful as potassium channel modulators. More specifically the invention provides chemical compounds useful as modulators of $SK_{Ca}$ and/or $IK_{Ca}$ channels.

11 Claims, No Drawings

POTASSIUM CHANNEL MODULATORS

TECHNICAL FIELD

This invention relates to novel compounds useful as potassium channel modulators. More specifically the invention provides chemical compounds useful as modulators of $SK_{Ca}$ and/or $IK_{Ca}$ channels.

BACKGROUND ART

Ion channels are transmembrane proteins, which catalyse the transport of inorganic ions across cell membranes. The ion channels participate in processes as diverse as the generation and timing of action potentials, synaptic transmissions, secretion of hormones, contraction of muscles, etc.

Two types of $Ca^{2+}$-activated potassium channels have been described from lymphocytes: 1) Small-conductance, apamin-sensitive, $Ca^{2+}$-activated K-channels ($SK_{Ca}$) and 2) Intermediate-conductance, inwardly rectifying, Clotrimazole-sensitive, $Ca^{2+}$-activated K-channels ($IK_{Ca}$), also referred to as Gardos-channels.

WO 97/34589 describes triaryl methane compounds that inhibit mammalian cell proliferation, inhibit the Gardos channel of erythrocytes, reduce sickle erythrocyte dehydration and/or delay the occurrence of erythrocyte sickling or deformation, and suggest the use of these compounds in abnormal cell proliferation.

WO 97/34599 describes the use of Clotrimazol and related compounds in the treatment of diarrhoea.

WO 00/50026 describes Gardos channel antagonists (i.e. $Ca^{2+}$-activated K-channels), which inhibit the Gardos channel of erythrocytes, reduce sickle erythrocyte dehydration and/or delay the occurrence of erythrocyte sickling or deformation.

WO 01/27070 describes the use of carbonylamino derivatives for treating CNS disorders relating to metabotropic glutamate receptor antagonists and/or agonists.

WO 01/49663 describes the use of certain substituted triarylmethane compounds for immunosuppressive treatment of autoimmune disorders or inflammatory diseases.

SUMMARY OF THE INVENTION

According to the present invention it has now been found that a particular group of chemical compounds possess valuable activity as modulators of $SK_{Ca}$ and/or $IK_{Ca}$ channels.

In its first aspect the invention provides chemical compounds characterized by the general Formula I

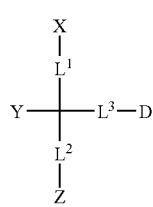

(I)

any of its enantiomers or any mixture of its enantiomers, or a pharmaceutically acceptable salt thereof, or an N-oxide thereof, wherein X and Y, independently of each another, represent a mono- or polycyclic, carbocyclic and/or heterocyclic group, which carbocyclic or heterocyclic groups optionally may be substituted one or more times with alkyl, alkenyl, alkynyl, hydroxy, alkoxy, amino, halogen, haloalkyl, nitro and/or cyano; and Z represents alkyl, alkenyl, alkynyl, cycloalkyl, cycloalkyl-alkyl, hydroxy-alkyl, cyano-alkyl, halo-alkyl, halo-alkenyl or halo-alkynyl, alkoxy, alkoxy-alkyl, alkoxy-alkoxy, alkoxy-alkoxy-alkyl, acyl, alkoxy-carbonyl, alkoxy-alkoxy-carbonyl, a malonic acid dialkyl ester, a diphenyl methyl group, or a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and $L^1$ and $L^2$, independently of each another, may be absent or represent divalent alkyl, alkenyl, alkynyl, O, S or $NR^9$; wherein $R^9$ represents hydrogen, alkyl, alkoxy or aryl; and $L^3$ may be absent or represents a linker of the formula —$(CH_2)_n$—Y—$(CH_2)_m$—, wherein n and m, independently of each another, represent 0, 1, 2, 3 or 4; and Y is absent or represents O, S, $NR^9$, wherein $R^9$ represents hydrogen, alkyl, alkoxy or aryl; and D represents alkyl, cycloalkyl, alkenyl, alkynyl or haloalkyl, or a group of the formula —$R^6$—$NR^5R^4$, —$R^6$—$NO_2$, —$R^6$—$OR^4$, —$R^6$—$SR^4$, —$R^6$—$S(=O)NR^5R^4$, —$R^6$—$S(=O)R^4$, —$R^6$—$S(=O)_2R^4$, —$R^6$—$S(=O)_2OR^4$, —$R^6$—$S(=O)_2NR^5R^4$, —$R^6$—$NR^5S(=O)_2R^4$, —$R^6$—$NR^7S(=O)_2NR^5R^4$, —$R^6$—CN, —$R^6$—$C(=NR^5)R^4$, —$R^6$—$C(=NNR^5)R^4$, —$R^6$—$C(=NOR^5)R^4$, —$R^6$—$C(=O)R^4$, —$R^6$—$C(=O)NR^5R^4$, —$R^6$—$C(=S)R^4$, —$R^6$—$C(=O)OR^4$, —$R^6$—$C(=S)OR^4$, —$R^6$—$C(=O)SR^4$, —$R^6$—$C(=S)SR^4$, —$R^6$—$C(=O)NR^5(OR^4)$, —$R^6$—$C(=S)NR^5(OR^4)$, —$R^6$—$C(=O)NR^5(SR^4)$, —$R^6$—$C(=S)NR^5(SR^4)$, —$R^6$—$CH(CN)_2$, —$R^6$—$NR^5C(=O)R^4$, —$R^6$—$NR^7C(=O)NR^5R^4$, —$R^6$—$C(=S)NR^5R^4$, —$R^6$—$CH[C(=O)R^4]_2$, —$R^6$—$CH[C(=S)R^4]_2$, —$R^6$—$CH[C(=O)OR^4]_2$, —$R^6$—$CH[C(=S)OR^4]_2$, —$R^6$—$CH[C(=O)SR^4]_2$, —$R^6$—$CH[C(=S)SR^4]_2$ or —$R^6$—$CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; or D represents a mono- or polycyclic, carbocyclic or heterocyclic group, which carbocyclic or heterocyclic group optionally may be substituted one or more times with alkyl, cycloalkyl, alkenyl, alkynyl, halogen, haloalkyl, aryl and heteroaryl, and/or a group of the formula —$R^6$—$NR^5R^4$, —$R^6$—$NO_2$, —$R^6$—$OR^4$, —$R^6$—$SR^4$, —$R^6$—$S(=O)NR^5R^4$, —$R^6$—$S(=O)R^4$, —$R^6$—$S(=O)_2R^4$, —$R^6$—$S(=O)_2OR^4$, —$R^6$—$S(=O)_2NR^5R^4$, —$R^6$—$NR^5S(=O)_2R^4$, —$R^6$—$NR^7S(=O)_2NR^5R^4$, —$R^6$—CN, —$R^6$—$C(=NR^5)R^4$, —$R^6$—$C(=NNR^5)R^4$, —$R^6$—$C(=NOR^5)R^4$, —$R^6$—$C(=O)R^4$, —$R^6$—$C(=O)NR^5R^4$, —$R^6$—$C(=S)$ $R^4$, $-R^6-C(=O)OR^4$, $-R^6-C(=S)OR^4$, $-R^6-C(=O)SR^4$, $-R^6-C(=S)SR^4$, $-R^6-C(=O)NR^5(OR^4)$, $-R^6-C(=S)NR^5(OR^4)$, $-R^6-C(=O)NR^5(SR^4)$, $-R^6-C(=S)NR^5(SR^4)$, $-R^6-CH(CN)_2$, $-R^6-C(=O)NR^5R^4$, $-R^6-NR^5C(=O)R^4$, $-R^6-NR^7C(=O)NR^5R^4$, $-R^6-C(=S)NR^5R^4$, $-R^6-CH[C(=O)R^4]_2$, $-R^6-CH[C(=S)R^4]_2$, $-R^6-CH[C(=O)OR^4]_2$, $-R^6-CH[C(=S)OR^4]_2$, $-R^6-CH[C(=O)SR^4]_2$, $-R^6-CH[C(=S)SR^4]_2$ or $-R^6-CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; or D represents $-S-R^1$, $-S(=O)-R^1$, $-S(=O)_2-R^1$, $-S(=O)-NR^2R^3$, $-S-C(=O)-R^1$, $-S-C(=O)-NR^2R^3$, $-O(C=O)-R^1$, $-O(C=O)-NR^2R^3$, $-N(C=O)-R^1$, $-N(C=O)-NR^2R^3$, $-P-(R^2R^3)$, $-P(=O)-R^1$, $-P(=O)-(R^2R^3)$, $-P(=O)_2-(R^2R^3)$; wherein $R^1$ represents alkyl, cycloalkyl, cycloalkyl-alkyl, alkenyl, alkynyl, haloalkyl, aryl, aralkyl, heteroaryl or heteroaryl-alkyl, which aromatic groups may optionally be substituted once or twice with halogen, alkyl, $CF_3$, nitro and/or cyano; or a group of the formula $-R^6-NR^5R^4$, $-R^6-NO_2$, $-R^6-OR^4$, $-R^6-SR^4$, $-R^6-S(=O)NR^5R^4$, $-R^6-S(=O)R^4$, $-R^6-S(=O)_2R^4$, $-R^6-S(=O)_2OR^4$, $-R^6-S(=O)_2NR^5R^4$, $-R^6-NR^5S(=O)_2R^4$, $-R^6-NR^7S(=O)_2NR^5R^4$, $-R^6-CN$, $-R^6-C(=NR^5)R^4$, $-R^6-C(=NNR^5)R^4$, $-R^6-C(=NOR^5)R^4$, $-R^6-C(=O)R^4$, $-R^6-C(=O)NR^5R^4$, $-R^6-C(=S)R^4$, $-R^6-C(=O)OR^4$, $-R^6-C(=S)OR^4$, $-R^6-C(=O)SR^4$, $-R^6-C(=S)SR^4$, $-R^6-C(=O)NR^5(OR^4)$, $-R^6-C(=S)NR^5(OR^4)$, $-R^6-C(=O)NR^5(SR^4)$, $-R^6-C(=S)NR^5(SR^4)$, $-R^6-CH(CN)_2$, $-R^6-NR^5C(=O)R^4$, $-R^6-NR^7C(=O)NR^5R^4$, $-R^6-C(=S)NR^5R^4$, $-R^6-CH[C(=O)R^4]_2$, $-R^6-CH[C(=S)R^4]_2$, $-R^6-CH[C(=O)OR^4]_2$, $-R^6-CH[C(=S)OR^4]_2$, $-R^6-CH[C(=O)SR^4]_2$, $-R^6-CH[C(=S)SR^4]_2$ or $-R^6-CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; and $R^2$ and $R^3$, independently of each another, represent hydrogen, hydroxy, alkyl or alkoxy; or $R^2$ and $R^3$, together with the phosphor atom to which they are bound, represent a heterocyclic ring; or $R^1$ represents a mono- or polycyclic, carbocyclic or heterocyclic group, which carbocyclic or heterocyclic group optionally may be substituted one or more times with alkyl, cycloalkyl, alkenyl, alkynyl, halogen, haloalkyl, aryl, heteroaryl and/or a group of the formula $-R^6-NR^5R^4$, $-R^6NO_2$, $-R^6-OR^4$, $-R^6-SR^4$, $-R^6-S(=O)NR^5R^4$, $-R^6-S(=O)R^4$, $-R^6-S(=O)_2R^4$, $-R^6-S(=O)_2OR^4$, $-R^6-S(=O)_2NR^5R^4$, $-R^6-NR^5S(=O)_2R^4$, $-R^6-NR^7S(=O)_2NR^5R^4$, $-R^6-CN$, $-R^6-C(=NR^5)R^4$, $-R^6-C(=NNR^5)R^4$, $-R^6-C(=NOR^5)R^4$, $-R^6-C(=O)R^4$, $-R^6-C(=O)NR^5R^4$, $-R^6-C(=S)R^4$, $-R^6-C(=O)OR^4$, $-R^6-C(=S)OR^4$, $-R^6-C(=O)SR^4$, $-R^6-C(=S)SR^4$, $-R^6-C(=O)NR^5(OR^4)$, $-R^6-C(=S)NR^5(OR^4)$, $-R^6-C(=O)NR^5(SR^4)$, $-R^6-C(=S)NR^5(SR^4)$, $-R^6-CH(CN)_2$, $-R^6-C(=O)NR^5R^4$, $-R^6-NR^5C(=O)R^4$, $-R^6-NR^7C(=O)NR^5R^4$, $-R^6-C(=S)NR^5R^4$, $-R^6-CH[C(=O)R^4]_2$, $-R^6-CH[C(=S)R^4]_2$, $-R^6-CH[C(=O)OR^4]_2$, $-R^6-CH[C(=S)OR^4]_2$, $-R^6-CH[C(=O)SR^4]_2$, $-R^6-CH[C(=S)SR^4]_2$ or $-R^6-CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; and $R^2$ and $R^3$, independently of each another, represent hydrogen, alkyl or alkoxy.

In another aspect the invention provides pharmaceutical compositions comprising a therapeutically effective amount of a chemical compound of the invention, or a pharmaceutically-acceptable addition salt thereof, together with at least one pharmaceutically-acceptable carrier or diluent.

In yet another aspect the invention relates to the use of a chemical compound of the invention, or a pharmaceutically-acceptable addition salt thereof, for the manufacture of a medicament.

In still another aspect the invention provides methods for treatment, prevention or alleviation of diseases or disorders or conditions responsive to modulation of $SK_{Ca}$ and/or $IK_{Ca}$ channels, which method comprises the step of administering to such a living animal body in need thereof a therapeutically effective amount of a compound of the invention or a pharmaceutically-acceptable addition salt thereof.

Other objects of the invention will be apparent to the person skilled in the art from the following detailed description and examples.

DETAILED DISCLOSURE OF THE INVENTION

Tertiary Triaryl Derivatives

In its first aspect the present invention provides tertiary triaryl derivative of Formula I

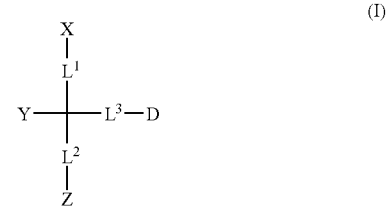

an enantiomer or any mixture of its enantiomers, or a pharmaceutically acceptable salt thereof, or an N-oxide thereof, wherein X and Y, independently of each another, represent a mono- or polycyclic, carbocyclic and/or heterocyclic group, which carbocyclic or heterocyclic groups optionally may be substituted one or more times with alkyl, alkenyl, alkynyl, hydroxy, alkoxy, amino, halogen, haloalkyl, nitro and/or cyano; and Z represents alkyl, alkenyl, alkynyl, cycloalkyl, cycloalkyl-alkyl, hydroxy-alkyl, cyano-alkyl, halo-alkyl, halo-alkenyl or halo-alkynyl, alkoxy, alkoxy-alkyl, alkoxy-alkoxy, alkoxy-alkoxy-alkyl, acyl, alkoxy-carbonyl, alkoxy-alkoxy-carbonyl, a malonic acid dialkyl ester, a diphenyl methyl group, or a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and $L^1$ and $L^2$, independently of each another, may be absent or represent divalent alkyl, alkenyl, alkynyl, O, S or $NR^9$; wherein $R^9$ represents hydrogen, alkyl, alkoxy or aryl; and $L^3$ may be absent or represents a linker of the formula $-(CH_2)_n-Y-(CH_2)_m-$, wherein n and m, independently of each another, represent 0, 1, 2, 3 or 4; and Y is absent or represents O, S, $NR^9$, wherein $R^9$ represents hydrogen, alkyl, alkoxy or aryl; and D represents alkyl, cycloalkyl, alkenyl, alkynyl or haloalkyl, or a group of the formula $-R^6-NR^5R^4$, $-R^6-NO_2$, $-R^6-OR^4$, $-R^6-SR^4$, $-R^6-S(=O)NR^5R^4$, $-R^6-S(=O)R^4$, $-R^6-S(=O)_2R^4$, $-R^6-S(=O)_2OR^4$, $-R^6-S(=O)_2NR^5R^4$, $-R^6-NR^5S(=O)_2R^4$, $-R^6-NR^7S(=O)_2NR^5R^4$, $-R^6-CN$, $-R^6-C(=NR^5)R^4$, $-R^6-C(=NNR^5)R^4$, $-R^6-C(=S)OR^4$, $-R^6-C(=O)R^4$, $-R^6-C(=O)NR^5R^4$, $-R^6-C(=S)R^4$, $-R^6-C(=O)OR^4$, $-R^6-C(=S)OR^4$, $-R^6-C(=O)SR^4$, $-R^6-C(=S)SR^4$, $-R^6-C(=O)NR^5(OR^4)$, $-R^6-C(=S)NR^5(OR^4)$, $-R^6-C(=O)NR^5(SR^4)$, $-R^6-C(=S)NR^5(SR^4)$, $-R^6-CH(CN)_2$, $-R^6-NR^5C(=O)R^4$, $-R^6-NR^7C(=O)NR^5R^4$, $-R^6-C(=S)NR^5R^4$, $-R^6-CH[C(=O)R^4]_2$, $-R^6-CH[C(=S)R^4]_2$, $-R^6-CH[C(=O)OR^4]_2$, $-R^6-CH[C(=S)OR^4]_2$, $-R^6-CH[C(=O)SR^4]_2$, $-R^6-CH[C(=S)SR^4]_2$ or $-R^6-CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; or D represents a mono- or polycyclic, carbocyclic or heterocyclic group, which carbocyclic or heterocyclic group optionally may be substituted one or more times with alkyl, cycloalkyl, alkenyl, alkynyl, halogen, haloalkyl, aryl and heteroaryl, and/or a group of the formula $-R^6-NR^5R^4$, $-R^6-NO_2$, $-R^6-OR^4$, $-R^6-SR^4$, $-R^6-S(=O)NR^5R^4$, $-R^6-S(=O)R^4$, $-R^6-S(=O)_2R^4$, $-R^6-S(=O)_2OR^4$, $-R^6-S(=O)_2NR^5R^4$, $-R^6-NR^5S(=O)_2R^4$, $-R^6-NR^7S(=O)_2NR^5R^4$, $-R^6-CN$, $-R^6-C(=NR^5)R^4$, $-R^6-C(=NNR^5)R^4$, $-R^6-C(=NOR^5)R^4$, $-R^6-C(=O)R^4$, $-R^6-C(=O)NR^5R^4$, $-R^6-C(=S)R^4$, $-R^6-C(=O)OR^4$, $-R^6-C(=S)OR^4$, $-R^6-C(=O)SR^4$, $-R^6-C(=S)SR^4$, $-R^6-C(=O)NR^5(OR^4)$, $-R^6-C(=S)NR^5(OR^4)$, $-R^6-C(=O)NR^5(SR^4)$, $-R^6-C(=S)NR^5(SR^4)$, $-R^6-CH(CN)_2$, $-R^6-NR^5C(=O)R^4$, $-R^6-NR^7C(=O)NR^5R^4$, $-R^6-C(=S)NR^5R^4$, $-R^6-CH[C(=O)R^4]_2$, $-R^6-CH[C(=S)R^4]_2$, $-R^6-CH[C(=O)OR^4]_2$, $-R^6-CH[C(=S)OR^4]_2$, $-R^6-CH[C(=O)SR^4]_2$, $-R^6-CH[C(=S)SR^4]_2$ or $-R^6-CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; or D represents $-S-R^1$, $-S(=O)-R^1$, $-S(=O)_2-R^1$, $-S(=O)-NR^2R^3$, $-S-C(=O)-R^1$, $-S-C(=O)-NR^2R^3$, $-O(C=O)-R^1$, $-O(C=O)-NR^2R^3$, $-N(C=O)-R^1$, $-N(C=O)-NR^2R^3$, $-P-(R^2R^3)$, $-P(=O)-R^1$, $-P(=O)-(R^2R^3)$, $-P(=O)_2-(R^2R^3)$; wherein $R^1$ represents alkyl, cycloalkyl, cycloalkyl-alkyl, alkenyl, alkynyl, haloalkyl, aryl, aralkyl, heteroaryl or heteroaryl-alkyl, which aromatic groups may optionally be substituted once or twice with halogen, alkyl, $CF_3$, nitro and/or cyano; or a group of the formula $-R^6-NR^5R^4$, $-R^6-NO_2$, $-R^6-OR^4$, $-R^6-SR^4$, $-R^6-S(=O)NR^5R^4$, $-R^6-S(=O)R^4$, $-R^6-S(=O)_2R^4$, $-R^6-S(=O)_2OR^4$, $-R^6-S(=O)_2NR^5R^4$, $-R^6-NR^5S(=O)_2R^4$, $-R^6-NR^7S(=O)_2NR^5R^4$, $-R^6-CN$, $-R^6-C(=NR^5)R^4$, $-R^6-C(=NNR^5)R^4$, $-R^6-C(=NOR^5)R^4$, $-R^6-C(=O)R^4$, $-R^6-C(=O)NR^5R^4$, $-R^6-C(=S)R^4$, $-R^6-C(=O)OR^4$, $-R^6-C(=S)OR^4$, $-R^6-C(=O)SR^4$, $-R^6-C(=S)SR^4$, $-R^6-C(=O)NR^5(OR^4)$, $-R^6-C(=S)NR^5(OR^4)$, $-R^6-C(=O)NR^5(SR^4)$, $-R^6-C(=S)NR^5(SR^4)$, $-R^6-CH(CN)_2$, $-R^6-NR^5C(=O)R^4$, $-R^6-NR^7C(=O)NR^5R^4$, $-R^6-C(=S)NR^5R^4$, $-R^6-CH[C(=O)R^4]_2$, $-R^6-CH[C(=S)R^4]_2$, $-R^6-CH[C(=O)OR^4]_2$, $-R^6-CH[C(=S)OR^4]_2$, $-R^6-CH[C(=O)SR^4]_2$, $-R^6-CH[C(=S)SR^4]_2$, or $-R^6-CH[C(=S)NR^5R^4]_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; and $R^2$ and $R^3$, independently of each another, represent hydrogen, hydroxy, alkyl or alkoxy; or $R^2$ and $R^3$, together with the phosphor atom to which they are bound, represent a heterocyclic ring; or $R^1$ represents a mono- or polycyclic, carbocyclic or heterocyclic group, which carbocyclic or heterocyclic group optionally may be substituted one or more times with alkyl, cycloalkyl, alkenyl, alkynyl, halogen, haloalkyl, aryl, heteroaryl and/or a group of the formula $-R^6-NR^5R^4$, $-R^6-NO_2$, $-R^6-OR^4$, $-R^6-SR^4$, $-R^6-S(=O)NR^5R^4$, $-R^6-S(=O)R^4$, $-R^6-S(=O)_2R^4$, $-R^6-S(=O)_2OR^4$, $-R^6-S(=O)_2NR^5R^4$, $-R^6-NR^5S(=O)_2R^4$, $-R^6-NR^7S(=O)_2NR^5R^4$, $-R^6-CN$, $-R^6-C(=NR^5)R^4$, $-R^6-C(=NNR^5)R^4$, $-R^6-C(=NOR^5)R^4$, $-R^6-C(=O)R^4$, $-R^6-C(=O)NR^5R^4$, $-R^6-C(=S)R^4$, $-R^6-C(=O)OR^4$, $-R^6-C(=S)OR^4$, —$R^6$—C(=O)$SR^4$, —$R^6$—C(=S)$SR^4$, —$R^6$—C(=O)$NR^5(OR^4)$, —$R^6$—C(=S)$NR^5(OR^4)$, —$R^6$—C(=O)$NR^5(SR^4)$, —$R^6$—C(=S)$NR^5(SR^4)$, —$R^6$—CH(CN)$_2$, —$R^6$—C(=O)$NR^5R^4$, —$R^6$—$NR^5$C(=O)$R^4$, —$R^6$—$NR^7$C(=O)$NR^5R^4$, —$R^6$—C(=S)$NR^5R^4$, —$R^6$—CH[C(=O)$R^4$]$_2$, —$R^6$—CH[C(=S)$R^4$]$_2$, —$R^6$—CH[C(=O)$OR^4$]$_2$, —$R^6$—CH[C(=S)$OR^4$]$_2$, —$R^6$—CH[C(=O)$SR^4$]$_2$, —$R^6$—CH[C(=S)$SR^4$]$_2$ or —$R^6$—CH[C(=S)$NR^5R^4$]$_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; and $R^2$ and $R^3$, independently of each another, represent hydrogen, alkyl or alkoxy.

In a more preferred embodiment $L^1$ and $L^2$ are absent; and $L^3$ is absent or represents a linker of the formula —Y—, wherein Y represents O, S or $NR^9$, wherein $R^9$ represents hydrogen or alkyl; and D represents —S—$R^1$, —S(=O)—$R^1$, —S(=O)$_2$—$R^1$, —S(=O)—$NR^2R^3$, —S—C(=O)—$R^1$, —S—C(=O)—$NR^2R^3$, —O(C=O)—$R^1$, —O(C=O)—$NR^2R^3$, —N(C=O)—$R^1$, —N(C=O)—$NR^2R^3$, —P—$(R^1)_2$, —P($R^2R^3$), —P(=O)—$R^1$, —P(=O)—$(R^2R^3)$, —P(=O)$_2$—$(R^1)_2$ or —P(=O)—$(OR^1)_2$; wherein $R^1$ represents alkyl, cycloalkyl, cycloalkyl-alkyl, alkenyl, alkynyl, haloalkyl, or a group of the formula —$R^6$—$NR^5R^4$, —$R^6$—$NO_2$, —$R^6$—$OR^4$, —$R^6$—$SR^4$, —$R^6$—S(=O)$NR^5R^4$, —$R^6$—S(=O)$R^4$, —$R^6$—S(=O)$_2R^4$, —$R^6$—S(=O)$_2OR^4$, —$R^6$—S(=O)$_2NR^5R^4$, —$R^6$—$NR^5$S(=O)$_2R^4$, —$R^6$—$NR^7$S(=O)$_2NR^5R^4$, —$R^6$—CN, —$R^6$—C(=$NR^5$)$R^4$, —$R^6$—C(=$NNR^5$)$R^4$, —$R^6$—C(=$NOR^5$)$OR^4$, —$R^6$—C(=O)$R^4$, —$R^6$—C(=O)$NR^5R^4$, —$R^6$—C(=S)$R^4$, —$R^6$—C(=O)$OR^4$, —$R^6$—C(=S)$OR^4$, —$R^6$—C(=O)$SR^4$, —$R^6$—C(=S)$SR^4$, —$R^6$—C(=O)$NR^5(OR^4)$, —$R^6$—C(=S)$NR^5(OR^4)$, —$R^6$—C(=O)$NR^5(SR^4)$, —$R^6$—C(=S)$NR^5(SR^4)$, —$R^6$—CH(CN)$_2$, —$R^6$—$NR^5$C(=O)$R^4$, —$R^6$—$NR^7$C(=O)$NR^5R^4$, —$R^6$—C(=S)$NR^5R^4$, —$R^6$—CH[C(=O)$R^4$]$_2$, —$R^6$—CH[C(=S)$R^4$]$_2$, —$R^6$—CH[C(=O)$OR^4$]$_2$, —$R^6$—CH[C(=S)$OR^4$]$_2$, —$R^6$—CH[C(=O)$SR^4$]$_2$, —$R^6$—CH[C(=S)$SR^4$]$_2$ or —$R^6$—CH[C(=S)$NR^5R^4$]$_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with with halogen, alkyl, $CF_3$, nitro and/or cyano; or $R^4$ and $R^5$, together with the atoms to which they are bound, form a heterocyclic ring, and $R^7$ is as defined above; and $R^6$ is absent or represents a linker selected from alkyl, alkenyl, alkynyl, cycloalkyl, aryl and heteroaryl; and $R^2$ and $R^3$, independently of each another, represent hydrogen, hydroxy, alkyl or alkoxy; or $R^2$ and $R^3$, together with the phosphor atom to which they are bound, represent a heterocyclic ring; or $R^1$ represents a mono- or polycyclic, carbocyclic or heterocyclic group, which carbocyclic or heterocyclic group optionally may be substituted one or more times with alkyl, cycloalkyl, alkenyl, alkynyl, halogen, haloalkyl, aryl, heteroaryl and/or a group of the formula —$R^6$—$NR^5R^4$, —$R^6$—$NO_2$, —$R^6$—$OR^4$, —$R^6$—$SR^4$, —$R^6$—S(=O)$NR^5R^4$, —$R^6$—S(=O)$R^4$, —$R^6$—S(=O)$_2R^4$, —$R^6$—S(=O)$_2OR^4$, —$R^6$—S(=O)$_2NR^5R^4$, —$R^6$—$NR^5$S(=O)$_2R^4$, —$R^6$—$NR^7$S(=O)$_2NR^5R^4$, —$R^6$—CN, —$R^6$—C(=$NR^5$)$R^4$, —$R^6$—C(=$NNR^5$)$R^4$, —$R^6$—C(=$NOR^5$)$OR^4$, —$R^6$—C(=O)$R^4$, —$R^6$—C(=O)$NR^5R^4$, —$R^6$—C(=S)$R^4$, —$R^6$—C(=O)$OR^4$, —$R^6$—C(=S)$OR^4$, —$R^6$—C(=O)$SR^4$, —$R^6$—C(=S)$SR^4$, —$R^6$—C(=O)$NR^5(OR^4)$, —$R^6$—C(=S)$NR^5(OR^4)$, —$R^6$—C(=O)$NR^5(SR^4)$, —$R^6$—C(=S)$NR^5(SR^4)$, —$R^6$—CH(CN)$_2$, —$R^6$—C(=O)$NR^5R^4$, —$R^6$—$NR^5$C(=O)$R^4$, —$R^6$—$NR^7$C(=O)$NR^5R^4$, —$R^6$—C(=S)$NR^5R^4$, —$R^6$—CH[C(=O)$R^4$]$_2$, —$R^6$—CH[C(=S)$R^4$]$_2$, —$R^6$—CH[C(=O)$OR^4$]$_2$, —$R^6$—CH[C(=S)$OR^4$]$_2$, —$R^6$—CH[C(=O)$SR^4$]$_2$, —$R^6$—CH[C(=S)$SR^4$]$_2$ or —$R^6$—CH[C(=S)$NR^5R^4$]$_2$; wherein $R^4$, $R^5$ and $R^7$, independently of each another, represent hydrogen, alkyl, alkenyl, alkynyl, cycloalkyl, aryl or heteroaryl, which aromatic group may optionally be substituted once or twice with halogen, alkyl, $CF_3$, nitro and/or cyano; or $R^4$ and $R^5$, together with the atoms to which they are bound, form a heterocyclic ring, and $R^7$ is as defined above; and R is absent or represents a linker selected from alkyl, alkenyl, alkynyl, cycloalkyl, aryl and heteroaryl; and $R^2$ and $R^3$, independently of each another, represent hydrogen or alkyl.

In a yet more preferred embodiment,

X, Y and Z represent a phenyl group, which phenyl groups, independently of each another, are optionally substituted one or more times with alkyl, alkenyl, alkynyl, hydroxy, alkoxy, amino, halogen, haloalkyl, nitro and/or cyano; or X and Y represent a phenyl group, which phenyl groups, independently of each another, are optionally substituted one or more times with alkyl, alkenyl, alkynyl, hydroxy, alkoxy, amino, halogen, haloalkyl, nitro and/or cyano; and Z represents alkyl, alkenyl, alkynyl, cycloalkyl, cycloalkyl-alkyl, hydroxy-alkyl, cyano-alkyl, halo-alkyl, halo-alkenyl, halo-alkynyl, alkoxy, alkoxy-alkyl, alkoxy-alkoxy, alkoxy-alkoxy-alkyl, acyl, alkoxy-carbonyl, alkoxy-alkoxy-carbonyl, a malonic acid dialkyl ester or a diphenyl methyl group; or X and Y represent a phenyl group, which phenyl groups, independently of each another, are optionally substituted one or more times with alkyl, alkenyl, alkynyl, hydroxy, alkoxy, amino, halogen, haloalkyl, nitro and/or cyano; and Z represents a heteroaryl group, which heteroaryl is optionally substituted one or more times with alkyl, alkenyl, alkynyl, hydroxy, alkoxy, amino, halogen, haloalkyl, nitro and/or cyano; or one of X and Y represents a phenyl group, which phenyl group is optionally substituted one or more times with alkyl, alkenyl, alkynyl, hydroxy, alkoxy, amino, halogen, haloalkyl, nitro and/or cyano; and the other of X and Y represents a heteroaryl group, which heteroaryl is optionally substituted one or more times with alkyl, alkenyl, alkynyl, hydroxy, alkoxy, amino, halogen, haloalkyl, nitro and/or cyano; and Z represents alkyl, alkenyl, alkynyl, cycloalkyl, cycloalkyl-alkyl, hydroxy-alkyl, cyano-alkyl, halo-alkyl, halo-alkenyl, halo-alkynyl, alkoxy, alkoxy-alkyl, alkoxy-alkoxy, alkoxy-alkoxy-alkyl, acyl, alkoxy-carbonyl, alkoxy-alkoxy-carbonyl, a malonic acid dialkyl ester or a diphenyl methyl group; or one of X and Y represents a phenyl group, which phenyl group is optionally substituted one or more times with alkyl, alkenyl, alkynyl, hydroxy, alkoxy, amino, halogen, haloalkyl, nitro and/or cyano; and Z and the other of X and Y represents a heteroaryl group, which heteroaryl is optionally substituted one or more times with alkyl, alkenyl, alkynyl, hydroxy, alkoxy, amino, halogen, haloalkyl, nitro and/or cyano.

In an even more preferred embodiment, the heteroaryl group is thiazolyl, in particular 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; pyrrolyl (azolyl), in particular 1, 2 or 3-pyrrolyl; [1,3,2]dioxaphospholane or [1,3,2]dioxaphosphinane.

In a still more preferred embodiment

X, Y and Z represent a phenyl group, which phenyl groups, independently of each another, optionally are substituted one or more times with halogen, in particular fluoro and/or chloro; alkyl, in particular methyl, ethyl, propyl and/or isopropyl; haloalkyl, in particular $CF_3$; nitro and/or cyano; or X and Y represent a phenyl group, which phenyl groups, independently of each another, optionally are substituted one or more times with halogen, in particular fluoro and/or chloro; alkyl, in particular methyl, ethyl, propyl and/or isopropyl; haloalkyl, in particular $CF_3$; nitro and/or cyano; and Z represents alkyl, alkenyl, alkynyl, cycloalkyl, cycloalkyl-alkyl, hydroxy-alkyl, cyano-alkyl, alkoxy, alkoxy-alkyl, alkoxy-alkoxy, alkoxy-alkoxy-alkyl, acyl, alkoxy-carbonyl, malonic acid dialkyl ester or a diphenyl methyl group; or X and Y represent a phenyl group, which phenyl groups, independently of each another, optionally are substituted one or more times with halogen, in particular fluoro and/or chloro; alkyl, in particular methyl, ethyl, propyl and/or isopropyl; haloalkyl, in particular $CF_3$; nitro and/or cyano; and Z represents 2-thiazolyl, 4-thiazolyl, 2-imidazolyl, 2-oxazolyl, 2-pyridinyl or [1,3,2]dioxaphospholane, which aromatic groups may be substituted one or more times with halogen, in particular fluoro and/or chloro; alkyl, in particular methyl, ethyl, propyl and/or isopropyl; haloalkyl, in particular $CF_3$; nitro and/or cyano; or one of X and Y represents a phenyl group, which phenyl group is optionally substituted one or more times with halogen, in particular fluoro and/or chloro; alkyl, in particular methyl, ethyl, propyl and/or isopropyl; haloalkyl, in particular $CF_3$; nitro and/or cyano; and the other of X and Y represents 2-thiazolyl, 4-thiazolyl, 2-imidazolyl, 2-oxazolyl, 2-pyridinyl or [1,3,2]dioxaphospholane, which aromatic groups may be substituted one or more times with halogen, in particular fluoro and/or chloro; alkyl, in particular methyl, ethyl, propyl and/or isopropyl; haloalkyl, in particular $CF_3$; nitro and/or cyano; and Z represents alkyl, alkenyl, alkynyl, cycloalkyl, cycloalkyl-alkyl, hydroxy-alkyl, cyano-alkyl, alkoxy, alkoxy-alkyl, alkoxy-alkoxy, alkoxy-alkoxy-alkyl, acyl, alkoxy-carbonyl, malonic acid dialkyl ester or a diphenyl methyl group; or one of X and Y represents a phenyl group, which phenyl group is optionally substituted one or more times with halogen, in particular fluoro and/or chloro; alkyl, in particular methyl, ethyl, propyl and/or isopropyl; haloalkyl, in particular $CF_3$; nitro and/or cyano; and Z and the other of X and Y represents 2-thiazolyl, 4-thiazolyl, 2-imidazolyl, 2-oxazolyl, 2-pyridinyl or [1,3,2] dioxaphospholane, which aromatic groups may be substituted one or more times with halogen, in particular fluoro and/or chloro; alkyl, in particular methyl, ethyl, propyl and/or isopropyl; haloalkyl, in particular $CF_3$; nitro and/or cyano.

In a still more preferred embodiment

D represents a phenyl group, which phenyl groupis substituted once or twice with halogen, in particular fluoro and/or chloro; alkyl, in particular methyl, ethyl, propyl and/or isopropyl; haloalkyl, in particular $CF_3$; nitro and/or cyano; or D represents a heteroaryl group selected from 2-thiazolyl, 4-thiazolyl, 2-imidazolyl, 2-oxazolyl or 2-pyridinyl, which heteroaryl group may be substituted once or twice with halogen, in particular fluoro and/or chloro; alkyl, in particular methyl, ethyl, propyl and/or isopropyl; haloalkyl, in particular $CF_3$; hydroxy, nitro and/or cyano; and $L^3$ is absent or represents a linker of the formula —Y—, wherein Y represents O or S.

In a still more preferred embodiment the phenyl groups and/or the heteroaryl groups are substituted once or twice with fluoro, chloro, $CF_3$, nitro and/or cyano.

In a most preferred embopdiment the compound of the invention is

2-[Bis-(4-fluoro-phenyl)-(4-nitro-3-trifluoromethyl-phenoxy)-methyl]-thiazole;

2-[Tris-(4-fluoro-phenyl)-methylsulfanyl]-pyridin-1-ol;

1-Methyl-2-[tris-(4-fluoro-phenyl)-methylsulfanyl]-1H-imidazole;

2-[Tris-(4-fluoro-phenyl)-methylsulfanyl]-pyridine;

2-[(2-Fluoro-phenyl)-bis-(4-fluoro-phenyl)-methoxy]-[1,3,2]-dioxaphospholane; or 2-[Tris-(4-fluoro-phenyl)-methoxy]-[1,3,2]-dioxaphospholane;

any of its enantiomers or any mixture of enantiomers, or a pharmaceutically acceptable salt thereof, or an N-oxide thereof.

In a still more preferred embodiment

D represents —CN, $R^6$—CN, —CON($R^2R^3$), —S—$R^1$, —S(=O)—$R^1$, —S(=O)$_2$—$R^1$, —S—C(=O)—$R^1$, —O(C=O)—$R^1$, —P—($R^2R^3$), —P(=O)($R^2R^3$), —P(=O)$_2$($R^2R^3$); wherein $R^1$ represents alkyl, cycloalkyl, cycloalkyl-alkyl or —$NR^5R^4$; wherein $R^4$ and $R^5$, independently of each another, represent hydrogen, alkyl, cycloalkyl, aryl or heteroaryl, which aromatic group may optionally be substituted once or twice with halogen, alkyl, $CF_3$, nitro and/or cyano; or $R^4$ and $R^5$, together with the N atom to which they are bound, form a pyrrolidine or piperidine ring; or $R^1$ represents aryl, aralkyl, heteroaryl, heteroaryl-alkyl, which aromatic groups may optionally be substituted once or twice with halogen, alkyl, $CF_3$, nitro and/or cyano; and $R^2$ and $R^3$, independently of each another, represent hydrogen, alkyl or alkoxy; or $R^2$ and $R^3$, together with the phosphor atom to which they are bound, represent a heterocyclic ring selected from [1,3,2]dioxaphospholane and [1,3,2]dioxaphosphinane; and $R^6$ is absent or represents alkyl.

In a still more preferred embodiment $L^3$ is absent or represents —O— or —S—.

In a still more preferred embodiment X and Y represent a phenyl group, which phenyl groups, independently of each another, optionally are substituted one or more times with halogen, in particular fluoro and/or chloro; alkyl, in particular methyl, ethyl, propyl and/or isopropyl; haloalkyl, in particular $CF_3$; nitro and/or cyano;

Z represents alkyl, alkenyl, alkynyl, cycloalkyl, cycloalkyl-alkyl, hydroxy-alkyl, cyano-alkyl, alkoxy, alkoxy-alkyl, alkoxy-alkoxy, alkoxy-alkoxy-alkyl, acyl, alkoxy-carbonyl, malonic acid dialkyl ester or a diphenyl methyl group; and D represents —CN, $R^6$—CN, —CON($R^2R^3$), wherein $R^2$ and $R^3$, independently of each another, represent hydrogen or alkyl; and $R^6$ represents alkyl.

In a most preferred embodiment compound of the invention is 2-(2-Fluoro-phenyl)-2-(4-fluoro-phenyl)-pent-4-enenitrile;

2-(2-Fluoro-phenyl)-2-(4-fluoro-phenyl)-3-methyl-butyronitrile;

2,2-Bis-(4-fluoro-phenyl)-3-methyl-butyronitrile;

2,2-Bis-(4-fluoro-phenyl)-4-methyl-pentanenitrile;

2,2-Bis-(4-fluoro-phenyl)-pent-4-enenitrile;

2,2-Bis-(4-fluoro-phenyl)-pent-4-ynenitrile;

2-(2-Fluoro-phenyl)-2-(4-fluoro-phenyl)-pent-4-ynenitrile;

2-(2-Fluoro-phenyl)-2-(4-fluoro-phenyl)-4-methyl-pentanenitrile;

2,2-Bis-(4-fluoro-phenyl)-3,3-diphenyl-propionitrile;

2-(2-Fluoro-phenyl)-2-(4-fluoro-phenyl)-3,3-diphenyl-propionitrile;

2-(3-Fluoro-phenyl)-2-(4-fluoro-phenyl)-3-methyl-butyronitrile;

2-(3-Fluoro-phenyl)-2-(4-fluoro-phenyl)-4-methyl-pentanenitrile;

2-(3-Fluoro-phenyl)-2-(4-fluoro-phenyl)-pent-4-enenitrile;

2-(3-Fluoro-phenyl)-2-(4-fluoro-phenyl)-pent-4-ynenitrile;

2,2-Bis-(4-fluoro-phenyl)-3-oxo-butyronitrile;

3-Ethoxy-2-(4-fluoro-phenyl)-2-(2-fluoro-phenyl)-propionitrile;

3-Cyano-3-(4-fluoro-phenyl)-3-(2-fluoro-phenyl)-propionic acid ethyl ester;

3-Ethoxy-2,2-bis-(4-fluoro-phenyl)-propionitrile;

3-Cyano-3,3-bis-(4-fluoro-phenyl)-propionic acid ethyl ester;

Cyano-(4-fluoro-phenyl)-(2-fluoro-phenyl)-acetic acid methyl ester;

2-[Cyano-bis-(4-fluoro-phenyl)-methyl]-malonic acid diethyl ester;

2,2-Bis-(4-fluoro-phenyl)-4-hydroxy-butyronitrile;

2,2-Bis-(4-fluoro-phenyl)-3-(2-methoxy-ethoxy)-propionitrile;

2,2-Bis-(4-fluoro-phenyl)-succinonitrile; or 2,2-Bis-(4-fluoro-phenyl)-3-methyl-butyramide;

any of its enantiomers or any mixture of enantiomers, or a pharmaceutically acceptable salt thereof, or an N-oxide thereof.

In a second preferred embodiment, the chemical compound of the invention is represented by the following Formula IV (Type 4)

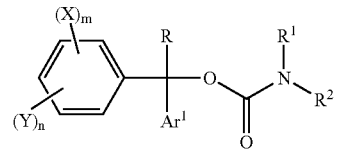

wherein m is 0, 1 or 2;

n is 0, 1 or 2;

X and Y, independently of each another, represent alkyl, alkenyl, alkynyl, hydroxy, alkoxy, amino, halogen, haloalkyl, nitro and/or cyano;

$Ar^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group ($Ar^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen or alkyl; or $R^1$ and $R^2$, together with the N atom to which they are bound, form a 5- to 7-membered heterocyclic ring.

In a more preferred embodiment m is 0 or 1;

n is 0 or 1;

X and Y, independently of each another, represent halogen, alkyl, $CF_3$, nitro and/or cyano;

$Ar^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen or alkyl; or $R^1$ and $R^2$, together with the N atom to which they are bound, form a pyrrolidine or a piperidine ring.

In a yet more preferred embodiment m is 0 or 1;

n is 0 or 1;

X and Y, independently of each another, represent halogen, alkyl, $CF_3$, nitro and/or cyano;

$Ar^1$ represents phenyl, which may be substituted once or twice with halogen, alkyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or R represents alkyl, alkenyl, cycloalkyl, cycloalkyl-alkyl or halo-alkyl; and $R^1$ and $R^2$, independently of each another, represent hydrogen or alkyl; or $R^1$ and $R^2$, together with the N atom to which they are bound, form a pyrrolidine or a piperidine ring.

In a still more preferred embodiment m is 0 or 1;

n is 0 or 1;

X and Y, independently of each another, represent fluoro, chloro, $CF_3$, nitro and/or cyano;

$Ar^1$ represents phenyl, which may be substituted once or twice with fluoro, chloro, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with fluoro, chloro, $CF_3$, nitro and/or cyano; or R represents alkyl, cycloalkyl or cycloalkyl-alkyl; and $R^1$ and $R^2$, independently of each another, represent hydrogen or alkyl; or $R^1$ and $R^2$, together with the N atom to which they are bound, form a pyrrolidine or a piperidine ring.

In a most preferred embodiment the chemical compound of the invention is (±)-Carbamic acid tris-(4-fluorophenyl)-methyl ester;

(±)-Carbamic acid cyclohexyl-bis-(4-fluorophenyl)-methyl ester;

(±)-Carbamic acid cyclohexyl-(4-fluorophenyl)-thiazol-2-yl-methyl ester;

(±)-Piperidine-1-carboxylic acid tris-(4-fluorophenyl)-thiazol-2-yl-methyl ester;

(±)-Methyl-carbamic acid cyclopentyl-bis-(4-fluorophenyl)-methyl ester;

(±)-Pyrrolidine-1-carboxylic acid cyclohexyl-bis-(4-fluorophenyl)-methyl ester;

(±)-Methyl-carbamic acid tris-(4-fluorophenyl)-methyl ester;

(±)-Methyl-carbamic acid cyclohexyl-(2-fluorophenyl)-(4-fluorophenyl)-methyl ester;

(±)-Carbamic acid cyclohexyl-(4-fluorophenyl)-pyridin-2-yl-methyl ester;

(±)-Dimethyl-carbamic acid tris-(4-fluorophenyl)-methyl ester;

(±)-Carbamic acid (2-fluorophenyl)-bis-(4-fluorophenyl)-methyl ester; or (±)-Carbamic acid (2-fluorophenyl)-(4-fluorophenyl)-phenyl-methyl ester;

an enantiomer or a mixture of enantiomers, or a pharmaceutically acceptable salt thereof, or an N-oxide thereof.

In a third preferred embodiment the chemical compound of the invention is represented by the following Formula V (Type 5)

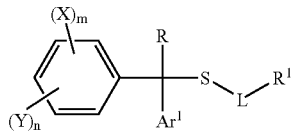

wherein n is 1 or 2;

m is 0, 1 or 2;

X and Y, independently of each another, represent alkyl, alkenyl, alkynyl, amino, halogen, haloalkyl, nitro and/or cyano;

$Ar^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group ($Ar^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkenyl or halo-alkynyl; and L is absent or represents alkyl; and $R^1$ represents alkyl, cycloalkyl or cycloalkyl-alkyl, —CN, —C(=O)$OR^4$, —C(=O)N($R^4R^5$), —C(=S)N($R^4R^5$), wherein $R^4$ and $R^5$, independently of each another, represent hydrogen, alkyl or phenyl, or $R^4$ and $R^5$, together with the nitrogen atom form a heterocyclic ring selected from pyrrolidinyl and piperidinyl, or a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano.

In a more preferred embodiment n is 1;

m is 0 or 1;

X and Y, independently of each another, represent halogen, alkyl, $CF_3$, nitro and/or cyano;

$Ar^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkenyl or halo-alkynyl; and L is absent or represents alkyl; and R$^1$ represents alkyl, cycloalkyl or cycloalkyl-alkyl, —CN, —C(=O)OR$^4$, —C(=O)N(R$^4$R$^5$), —C(=S)N(R$^4$R$^5$), wherein R$^4$ and R$^5$, independently of each another, represent hydrogen, alkyl or phenyl, or R$^4$ and R$^5$, together with the nitrogen atom form a heterocyclic ring selected from pyrrolidinyl and piperidinyl, or an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano.

In a yet more preferred embodiment m is 1;

n is 0 or 1;

X and Y, independently of each another, represent fluoro, chloro, CF$_3$, nitro and/or cyano;

Ar$^1$ represents phenyl, 2-thiazolyl, 4-thiazolyl, 2-imidazolyl, 2-oxazolyl or 2-pyridinyl, which aromatic group may be substituted once or twice with halogen, alkyl, CF$_3$, nitro and/or cyano;

Ar$^2$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, CF$_3$, nitro and/or cyano; or R represents alkyl, alkenyl, cycloalkyl or cycloalkyl-alkyl; and L is absent or represents methylene or ethylene; and R$^1$ represents alkyl, cycloalkyl or cycloalkyl-alkyl, —CN, —C(=O)OR$^4$, —C(=O)N(R$^4$R$^5$), —C(=S)N(R$^4$R$^5$), wherein R$^4$ and R$^5$, independently of each another, represent hydrogen, alkyl or phenyl, or R$^4$ and R$^5$, together with the nitrogen atom form a heterocyclic ring selected from pyrrolidinyl and piperidinyl, or an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, CF$_3$, nitro and/or cyano.

In a most preferred embodiment the chemical compound of the invention is

2-[Cyclohexyl-(4-fluorophenyl)-(2-fluorophenyl)-methylsulfanyl]-thiazole;

2-[(2-Chlorophenyl)-cyclohexyl-(4-fluorophenyl)-(2-fluorophenyl)-methylsulfanyl]-1-methyl-1H-imidazole;

2-[(4-Chlorophenylsulfanyl)-cyclopentyl-(4-fluorophenyl)-(2-fluorophenyl)-methyl]-pyridine;

2-[Cyclohexyl-(3,4-dichlorophenyl)-(1H-imidazol-2-yl)-methylsulfanyl]-pyridine;

2-[Cyclopentyl-(2-fluorothiazol-4-yl)-(4-nitro-3-trifluoromethylphenyl)-methylsulfanyl]-pyridine;

2-[(4-fluorophenyl)-(4-fluorophenylsulfanyl)-(4-nitro-3-trifluoromethylphenyl)-methyl]-thiazole;

2-[Cyclohexylsulfanyl-(4-fluorophenyl)-(4-nitro-3-trifluoromethylphenyl)-methyl]-thiazole;

2-[Cyclopentylsulfanyl-bis-(4-fluorophenyl)-methyl]-1-methyl-1H-imidazole;

4-[Cyclohexylsulfanyl-bis-(4-fluorophenyl)-methyl]-2-fluoro-thiazole;

2-[Bis-(4-fluorophenyl)-(2-fluorophenyl)-methylsulfonyl]-thiazole;

1-Methyl-2-[tris-(4-fluorophenyl)-methylsulfanyl]-1H-imidazole;

2-[Tris-(4-fluorophenyl)-methylsulfanyl]-pyridine;

2-[Tris-(4-fluorophenyl)-methylsulfanyl]-pyridine-N-oxide;

[Bis-(4-fluoro-phenyl)-(2-fluoro-phenyl)-methylsulfanyl]-acetonitrile;

2-[Bis-(4-fluoro-phenyl)-(2-fluoro-phenyl)-methylsulfanyl]-acetamide;

[(2-Fluoro-phenyl)-bis-(4-fluoro-phenyl)-methylsulfanyl]-acetic acid;

2-[Bis-(4-fluoro-phenyl)-(2-fluoro-phenyl)-methylsulfanyl]-propionamide;

2-[Bis-(4-fluoro-phenyl)-(2-fluoro-phenyl)-methylsulfanyl]-thioacetamide;

2-[Bis-(4-fluoro-phenyl)-(2-fluoro-phenyl)-methylsulfanyl]-N,N-diethyl-acetamide; or 2-[Bis-(4-fluoro-phenyl)-(2-fluoro-phenyl)-methylsulfanyl]-1-piperidin-1-yl-ethanone;

an enantiomer or a mixture of enantiomers, or a pharmaceutically acceptable salt thereof, or an N-oxide thereof.

In a fourth preferred embodiment the chemical compound of the invention is represented by the following Formula VI (Type 6)

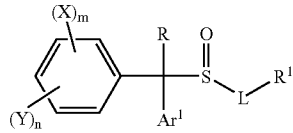

wherein m is 1 or 2;

n is 0, 1 or 2;

X and Y, independently of each another, represent alkyl, alkenyl, alkynyl, amino, halogen, haloalkyl, nitro and/or cyano;

Ar$^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group (Ar$^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and L is absent or represents alkyl; and R$^1$ represents cycloalkyl, or a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano.

In a more preferred embodiment m is 0 or 1;

n is 0 or 1;

X and Y, independently of each another, represent halogen, alkyl, CF$_3$, nitro and/or cyano;

Ar$^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl;

and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and L is absent or represents alkyl; and $R^1$ represents cycloalkyl or an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano.

In a yet more preferred embodiment
m is 0 or 1;
n is 0 or 1;
X and Y, independently of each another, represent fluoro, chloro, $CF_3$, nitro and/or cyano;

$Ar^1$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or R represents alkyl, alkenyl, cycloalkyl, cycloalkyl-alkyl, halo-alkyl; and L is absent or represents methylene or ethylene; and $R^1$ represents cycloalkyl or an aromatic group selected from phenyl, 2-thiazolyl, 4-thiazolyl, 2-imidazolyl, 2-oxazolyl and 2-pyridinyl, which aromatic groups may be substituted once or twice with halogen, methyl, $CF_3$, nitro and/or cyano.

In a still more preferred embodiment
m is 0 or 1;
n is 0 or 1;
X and Y, independently of each another, represent halogen, alkyl, $CF_3$, nitro and/or cyano;

$Ar^1$ represents an aromatic group selected from phenyl and 2-thiazolyl, which aromatic groups may be substituted once or twice with fluoro, $CF_3$, nitro and/or cyano;

$Ar^2$ represents phenyl, which may be substituted once or twice with fluoro, $CF_3$, nitro and/or cyano; or R represents cycloalkyl or cycloalkyl-alkyl; and L is absent or represents —$CH_2$—; and $R^1$ represents cycloalkyl, phenyl, 2-thiazolyl, 2-imidazolyl or 2-pyridinyl, which aromatic groups may be substituted once with fluoro, $CF_3$, nitro and/or cyano; or $R^1$ represents 2-thiazolyl-methyl.

In a most preferred embodiment the chemical compound of the invention is

Methyl tris(4-fluorophenyl)methyl sulfoxide (Compound 6-1);

Ethyl (bis(4-fluorophenyl)phenyl)methyl sulfoxide (Compound 6-2);

Cyclohexylmethyl tris(4-fluorophenyl)methyl sulfoxide (Compound 6-3);

Cyclohexyl tris(4-fluorophenyl)methyl sulfoxide (Compound 6-4);

Isopropyl tris(4-fluorophenyl)methyl sulfoxide (Compound 6-5);

(2-Thiazolyl)methyl tris(4-fluorophenyl)methyl sulfoxide (Compound 6-6);

Phenyl tris(4-fluorophenyl)methyl sulfoxide (Compound 6-7);

1-Methyl-2-imidazolyl tris(4-fluorophenyl)methyl) sulfoxide (Compound 6-8);

2-Pyridyl tris(4-fluorophenyl)methyl sulfoxide (Compound 6-9);

(Cyclohexyl-bis(4-fluorophenyl))methyl phenyl sulfoxide (Compound 6-10);

(Cyclopentyl-bis(4-fluorophenyl))methyl methyl sulfoxide (Compound 6-11); or (Cyclohexyl-(4-fluorophenyl)-(2-thiazolyl))methyl methyl sulfoxide (Compound 6-12);

an enantiomer or a mixture of enantiomers, or a pharmaceutically acceptable salt thereof, or an N-oxide thereof.

In a fifth preferred embodiment the chemical compound of the invention is represented by the following Formula VII (Type 7)

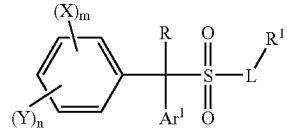

wherein
m is 1 or 2;
n is 0, 1 or 2;
X and Y, independently of each another, represent alkyl, alkenyl, alkynyl, hydroxy, alkoxy, amino, halogen, haloalkyl, nitro and/or cyano;

$Ar^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group ($Ar^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and L may be absent or represents alkyl; and $R^1$ represents alkyl, cycloalkyl or a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano.

In a more preferred embodiment
m is 1;
n is 0 or 1;
X and Y, independently of each another, represent halogen, alkyl, $CF_3$, nitro and/or cyano;

$Ar^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl;

oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and L may be absent or represents alkyl; and $R^1$ represents alkyl, cycloalkyl or an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano.

In a yet more preferred embodiment m is 1;

n is 0 or 1;

X and Y, independently of each another, represent fluoro, chloro, $CF_3$, nitro and/or cyano;

$Ar^1$ represents an aromatic group selected from phenyl, 2-thiazolyl, 4-thiazolyl, 2-imidazolyl, 2-oxazolyl and 2-pyridinyl, which aromatic groups may be substituted once or twice with fluoro, chloro, methyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with fluoro, chloro, methyl, $CF_3$, nitro and/or cyano; or R represents alkyl, alkenyl, cycloalkyl, cycloalkyl-alkyl, halo-alkyl; and L may be absent or represents methylene or ethylene; and $R^1$ represents alkyl, cycloalkyl or an aromatic group selected from phenyl, 2-thiazolyl, 4-thiazolyl, 2-imidazolyl, 2-oxazolyl and 2-pyridinyl, which aromatic groups may be substituted once or twice with fluoro, chloro, methyl, $CF_3$, nitro and/or cyano.

In a still more preferred embodiment m is 1;

n is 0 or 1;

X and Y, independently of each another, represent fluoro, chloro, $CF_3$, nitro and/or cyano;

$Ar^1$ represents an aromatic group selected from phenyl and 2-thiazolyl, which aromatic groups may be substituted once or twice with fluoro, chloro, methyl, $CF_3$, nitro and/or cyano;

$Ar^2$ represents phenyl, which may be substituted once or twice with fluoro, $CF_3$, nitro and/or cyano; or R represents alkyl, cycloalkyl or cycloalkyl-alkyl; and L may be absent or represents methylene; and $R^1$ represents alkyl or cycloalkyl; or $R^1$ represents phenyl, 2-thiazolyl, 2-imidazolyl or 2-pyridinyl, which aromatic groups may be substituted once or twice with fluoro, chloro, methyl, $CF_3$, nitro and/or cyano.

In a most preferred embodiment the chemical compound of the invention is

Methyl tris(4-fluorophenyl)methyl sulfone (Compound 7-1);

Ethyl (bis(4-fluorophenyl)phenyl)methyl sulfone (Compound 7-2);

Cyclohexylmethyl tris(4-fluorophenyl)methyl sulfone (Compound 7-3);

Cyclohexyl tris(4-fluorophenyl)methyl sulfone (Compound 7-4);

Isopropyl tris(4-fluorophenyl)methyl sulfone (Compound 7-5);

(2-Thiazolyl)methyl tris(4-fluorophenyl)methyl sulfone (Compound 7-6);

Phenyl tris(4-fluorophenyl)methyl sulfone (Compound 7-7);

1-Methyl-2-imidazolyl tris(4-fluorophenyl)methyl) sulfone (Compound 7-8);

2-Pyridyl tris(4-fluorophenyl)methyl sulfone (Compound 7-9);

(Cyclohexyl-bis(4-fluorophenyl))methyl phenyl sulfone (Compound 7-10);

(Cyclopentyl-bis(4-fluorophenyl))methyl methyl sulfone (Compound 7-11);

(Cyclohexyl-(4-fluorophenyl)-(2-thiazolyl))methyl methyl sulfone (Compound 7-12);

((2-Fluorophenyl)-bis(4-fluorophenyl)-phenyl)methyl methyl sulfone (Compound 7-13); or Methanesulphonyl-2-fluorophenyl-bis-(4-fluoro-phenyl) methane;

an enantiomer or a mixture of enantiomers, or a pharmaceutically acceptable salt thereof, or an N-oxide thereof.

In a sixth preferred embodiment the chemical compound of the invention is represented by Formula VIII (Type 8)

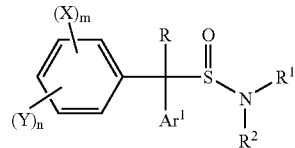

wherein m is 0, 1 or 2;

n is 0, 1 or 2;

X and Y, independently of each another, represent alkyl, alkenyl, alkynyl, hydroxy, alkoxy, amino, halogen, haloalkyl, nitro and/or cyano;

$Ar^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group ($Ar^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl, cycloalkyl, cycloalkyl-alkyl and/or a mono- or polycyclic, carbocyclic or heterocyclic group, which carbocyclic or heterocyclic groups optionally may be substituted one or more times with alkyl, alkenyl, alkynyl, hydroxy, alkoxy, amino, halogen, haloalkyl, nitro and/or cyano; or $R^1$ and $R^2$, together with the N atom to which they are bound, form a 5- to 7-membered heterocyclic ring.

In a more preferred embodiment m is 0 or 1;

n is 0 or 1;

X and Y, independently of each another, represent halogen, alkyl, $CF_3$, nitro and/or cyano;

$Ar^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl, cycloalkyl or cycloalkyl-alkyl, or an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or $R^1$ and $R^2$, together with the N atom to which they are bound, form a pyrrolidine or piperidine ring.

In a yet more preferred embodiment m is 0 or 1;

n is 0 or 1;

X and Y, independently of each another, represent halogen, alkyl, $CF_3$, nitro and/or cyano;

$Ar^1$ represents phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or R represents alkyl, alkenyl, cycloalkyl, cycloalkyl-alkyl or halo-alkyl; and $R^1$ and $R^2$, independently of each another, represent hydrogen, alkyl, cycloalkyl or cycloalkyl-alkyl, or an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or $R^1$ and $R^2$, together with the N atom to which they are bound, form a pyrrolidine or piperidine ring.

In a still more preferred embodiment m is 0 or 1;

n is 0 or 1;

X and Y, independently of each another, represent fluoro, $CF_3$, nitro and/or cyano;

$Ar^1$ represents phenyl, 2-thiazolyl, 4-thiazolyl, 2-imidazolyl, 2-oxazolyl and 2-pyridinyl, which aromatic groups may be substituted once or twice with fluoro, chloro, methyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with fluoro, chloro, methyl, $CF_3$, nitro and/or cyano; or R represents alkyl, alkenyl, cycloalkyl, cycloalkyl-alkyl or halo-alkyl; and $R^1$ and $R^2$, independently of each another, represent hydrogen, alkyl, cycloalkyl or cycloalkyl-alkyl, or 2-oxazolyl, which may be substituted with fluoro, methyl, $CF_3$, nitro or cyano; or $R^1$ and $R^2$, together with the N atom to which they are bound, form a pyrrolidine or piperidine ring.

In a most preferred embodiment the chemical compound of the invention is

Tris-(4-fluorophenyl)-methanesulfinic acid amide;

Bis-(4-fluorophenyl)-phenyl-methanesulfinic acid methylamide;

Tris-(4-fluorophenyl)-methanesulfinic acid cyclohexylamide;

1-[Tris-(4-fluorophenyl)-methanesulfinyl]-piperidine;

Tris-(4-fluorophenyl)-methanesulfinic acid dimethylamide;

Tris-(4-fluorophenyl)-methanesulfinic acid thiazol-2-ylamide;

Tris-(4-fluorophenyl )-methanesulfinic acid (4-fluorophenyl)-amide;

Bis-(4-fluorophenyl)-(1-methyl-1H-imidazol-2-yl)-methanesulfinic acid methylamide;

Cyclohexyl-(4-fluorophenyl)-thiazol-2-yl-methanesulfinic acid amide;

Bis-(4-fluorophenyl)-(1-methyl-1H-imidazol-2-yl)-methanesulfinic acid amide;

Bis-(4-fluorophenyl)-thiazol-2-yl-methanesulfinic acid amide; or

Bis-(4-fluorophenyl)-oxazol-2-yl-methanesulfinic acid amide;

an enantiomer or a mixture of enantiomers, or a pharmaceutically acceptable salt thereof, or an N-oxide thereof.

In a seventh preferred embodiment the chemical compound of the invention is represented by Formula IX (Type 9)

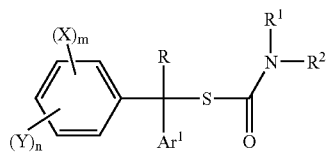

wherein m is 0, 1 or 2;

n is 0, 1 or 2;

X and Y, independently of each another, represent alkyl, alkenyl, alkynyl, hydroxy, alkoxy, amino, halogen, haloalkyl, nitro and/or cyano;

$Ar^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group ($Ar^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl, cycloalkyl, cycloalkyl-alkyl and/or a mono- or polycyclic, carbocyclic or heterocyclic group, which carbocyclic or heterocyclic groups optionally may be substituted one or more times with alkyl, alkenyl, alkynyl, hydroxy, alkoxy, amino, halogen, haloalkyl, nitro and/or cyano; or $R^1$ and $R^2$, together with the N atom to which they are bound, form a 5- to 7-membered heterocyclic ring.

In a more preferred embodiment m is 0 or 1;

n is 0 or 1;

X and Y, independently of each another, represent halogen, alkyl, $CF_3$, nitro and/or cyano;

$Ar^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl, cycloalkyl, cycloalkyl-alkyl and/or an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or $R^1$ and $R^2$, together with the N atom to which they are bound, form a pyrrolidine or a piperidine ring.

In a yet more preferred embodiment m is 0 or 1;

n is 0 or 1;

X and Y, independently of each another, represent fluoro, chloro, $CF_3$, nitro and/or cyano;

$Ar^1$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or R represents alkyl, alkenyl, cycloalkyl, cycloalkyl-alkyl or halo-alkyl; and $R^1$ and $R^2$, independently of each another, represent hydrogen, alkyl, cycloalkyl, cycloalkyl-alkyl and/or an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or $R^1$ and $R^2$, together with the N atom to which they are bound, form a pyrrolidine or a piperidine ring.

In a still more preferred embodiment m is 0 or 1;

n is 0 or 1;

X and Y, independently of each another, represent fluoro, $CF_3$, nitro and/or cyano;

$Ar^1$ represents phenyl or 2-thiazolyl, which may be substituted once with fluoro, chloro, methyl, $CF_3$, nitro or cyano;

$Ar^2$ represents phenyl, which may be substituted once with fluoro, $CF_3$, nitro or cyano; or R represents cycloalkyl or cycloalkyl-alkyl; and $R^1$ and $R^2$, independently of each another, represent hydrogen, alkyl, cycloalkyl, cycloalkyl-alkyl and/or an aromatic group selected from phenyl, 2-thiazolyl, 4-thiazolyl, 2-imidazolyl, 2-oxazolyl; or $R^1$ and $R^2$, together with the N atom to which they are bound, form a pyrrolidine or a piperidine ring.

In a most preferred embodiment the chemical compound of the invention is

Thiocarbamic acid S-[tris-(4-fluorophenyl)-methyl] ester;

Thiocarbamic acid S-[cyclohexyl-bis-(4-fluorophenyl)-methyl] ester;

Thiocarbamic acid S-[cyclohexyl-(4-fluorophenyl)-thiazol-2-yl-methyl] ester;

Piperidine-1-carbothioic acid S-[tris-(4-fluorophenyl)-methyl] ester;

Methyl-thiocarbamic acid S-[cyclopentyl-bis-(4-fluorophenyl)-methyl] ester;

Pyrrolidine-1-carbothioic acid S-[cyclohexyl-bis-(4-fluorophenyl)-methyl] ester;

Methyl-thiocarbamic acid S-[tris-(4-fluorophenyl)-methyl] ester;

Methyl-thiocarbamic acid S-[cyclopentyl-(2-fluorophenyl)-(4-fluorophenyl)-methyl] ester;

Thiocarbamic acid S-[cyclohexyl-(4-fluorophenyl)-pyridin-2-yl-methyl] ester;

Dimethyl-thiocarbamic acid S-[tris-(4-fluorophenyl)-methyl] ester;

Thiocarbamic acid S-[(2-fluorophenyl)-bis-(4-fluorophenyl)-methyl] ester; or

Thiocarbamic acid S-[(2-fluorophenyl)-(4-fluorophenyl)-phenyl-methyl] ester;

an enantiomer or a mixture of enantiomers, or a pharmaceutically acceptable salt thereof, or an N-oxide thereof.

In an eight preferred embodiment the chemical compound of the invention is represented by Formula X (Type 10)

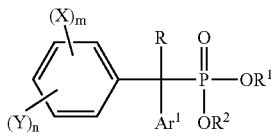

wherein m is 1 or 2;

n is 0, 1 or 2;

X and Y, independently of each another, represent alkyl, alkenyl, alkynyl, alkoxy, amino, halogen, haloalkyl, nitro and/or cyano;

$Ar^1$ represents a phenyl group substituted one or more times with alkyl, alkenyl, alkynyl, hydroxy, alkoxy, amino, halogen, haloalkyl, nitro and/or cyano; and R represents a group ($Ar^2$) which is a mono- or polycyclic, heterocyclic group other than imidazolyl, which carbocyclic or heterocyclic group may optionally be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl, cycloalkyl or cycloalkyl-alkyl; or $R^1$ and $R^2$ together with the phosphor and the oxygen atoms to which they are bound form a 5- to 7-membered heterocyclic ring.

In a more preferred embodiment m is 1;

n is 0 or 1;

X and Y, independently of each another, represent halogen, alkyl, $CF_3$, nitro and/or cyano;

$Ar^1$ represents a phenyl group substituted once or twice with halogen, alkyl, $CF_3$, nitro and/or cyano;

$Ar^2$ represents an aromatic group selected from phenyl, 2, 4 or 5-thiazolyl; isothiazolyl, in particular 3, 4 or 5-isothiazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, cycloalkyl, cycloalkyl-alkyl or halo-alkyl; and $R^1$ and $R^2$, independently of each another, represent alkyl, cycloalkyl or cycloalkyl-alkyl; or $R^1$ and $R^2$ together with the phosphor and the oxygen atoms to which they are bound form a 5-to 6-membered heterocyclic ring.

In a yet more preferred embodiment m is 1;

n is 0 or 1;

X and Y, independently of each another, represent fluoro, chloro, $CF_3$, nitro 5 and/or cyano;

$Ar^1$ represents phenyl, substituted once or twice with fluoro, chloro, $CF_3$, nitro and/or cyano;

$Ar^2$ represents an aromatic group selected from phenyl, 2-thiazolyl, 4-thiazolyl, 2-oxazolyl and 2-pyridinyl, which aromatic group optionally may be substituted once or twice with fluoro, chloro, methyl, $CF_3$, nitro and/or cyano; or R represents alkyl, alkenyl, cycloalkyl, cycloalkyl-alkyl or halo-alkyl; and $R^1$ and $R^2$, independently of each another, represent alkyl, cycloalkyl or cycloalkyl-alkyl; or $R^1$ and $R^2$ together with the phosphor and the oxygen atoms to which they are bound form a 5-membered heterocyclic dioxaphospholane ring.

In a still more preferred embodiment m is 1;

n is 0 or 1;

X and Y, independently of each another, represent fluoro, $CF_3$, nitro and/or cyano;

$Ar^1$ represents phenyl, which is substituted once or twice with fluoro, $CF_3$, nitro and/or cyano;

$Ar^2$ represents phenyl or 2-thiazolyl, which aromatic group may optionally be substituted once or twice with fluoro, methyl, $CF_3$, nitro and/or cyano; or R represents alkyl, cycloalkyl or cycloalkyl-alkyl; and $R^1$ and $R^2$, independently of each another, represent alkyl or cycloalkyl; or $R^1$ and $R^2$ together with the phosphor and the oxygen atoms to which they are bound form a 5-membered heterocyclic dioxaphospholane ring.

In a most preferred embodiment the chemical compound of the invention is

[Cyclohexyl-bis-(4-fluorophenyl)-methyl]-phosphonic acid dimethyl ester;

[Cyclopentyl-bis-(4-fluorophenyl)-methyl]-phosphonic acid dipropyl ester;

[1,1-Bis-(4-fluorophenyl)-hexyl]-phosphonic acid dimethyl ester;

[1,1-Bis-(4-fluorophenyl)-2-methyl-propyl]-phosphonic acid dimethyl ester;

[Bis-(4-fluorophenyl)-pyridin-2-yl-methyl]-phosphonic acid dimethyl ester;

[Bis-(4-fluorophenyl)-thiazol-2-yl-methyl]-phosphonic acid dimethyl ester;

[Tris-(4-fluoro-phenyl)-methyl]-phosphonic acid dimethyl ester;

[(2-Fluoro-phenyl)-bis-(4-fluoro-phenyl)-methyl]-phosphonic acid dimethyl ester;

[(2-Chloro-phenyl)-(2-fluoro-phenyl)-(4-fluoro-phenyl)-methyl]-phosphonic acid dimethyl ester;

[(4-Chloro-phenyl)-bis-(4-fluoro-phenyl)-methyl]-phosphonic acid dimethyl ester;

[Bis-(4-fluoro-phenyl)-(2-fluoro-phenyl)-methyl]-phosphonic acid; or

[Bis-(4-fluoro-phenyl)-p-tolyl-methyl]-phosphonic acid;

an enantiomers or a mixture of enantiomers, or a pharmaceutically acceptable salt thereof, or an N-oxide thereof.

In a ninth preferred embodiment the chemical compound of the invention is represented by Formula XII (Type 12)

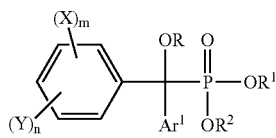

wherein m is 0, 1 or 2;

n is 0, 1 or 2;

X and Y, independently of each another, represent alkenyl, alkynyl, alkoxy, amino, halogen, haloalkyl, nitro and/or cyano;

$Ar^1$ represents a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; and R represents a group ($Ar^2$) which is a mono- or polycyclic, carbocyclic or heterocyclic group, which carbocyclic or heterocyclic group optionally may be substituted one or more times with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl or alkoxy; or $R^1$ and $R^2$ together with the phosphor and the oxygen atoms to which they are bound form a heterocyclic (dioxaphospholane) ring.

In a more preferred embodiment m is 0 or 1;

n is 0 or 1;

X and Y, independently of each another, represent halogen, $CF_3$, nitro and/or cyano;

$Ar^1$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano;

$Ar^2$ represents an aromatic group selected from phenyl; 2, 4 or 5-thiazolyl; isothiazolyl, in particular 3, 4 or 5-isothiazolyl; imidazolyl, in particular 1, 2 or 4-imidazolyl; oxazolyl, in particular 2, 4 or 5-oxazolyl; isoxazolyl, in particular 3, 4 or 5-isoxazolyl; pyridinyl, in particular 2, 3 or 4-pyridinyl; pyrimidinyl, in particular 2, 4 or 5-pyrimidinyl; and pyrrolyl (azolyl), in particular 1, 2 or 3-pyrrolyl; which aromatic group may be substituted once or twice with alkyl, alkenyl, alkynyl, hydroxy, alkoxy, amino, halogen, haloalkyl, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl or alkoxy; or $R^1$ and $R^2$ together with the phosphor and the oxygen atoms to which they are bound form a heterocyclic (dioxaphospholane) ring.

In a yet more preferred embodiment m is 0 or 1;

n is 0 or 1;

X and Y, independently of each another, represent halogen, $CF_3$, nitro and/or cyano;

$Ar^1$ represents phenyl, which may be substituted once or twice with halogen, alkyl, $CF_3$, nitro and/or cyano;

$Ar^2$ represents an aromatic group selected from phenyl, 2-thiazolyl, 4-thiazolyl, 2-imidazolyl, 2-oxazolyl and 2-pyridinyl, which aromatic groups may be substituted once or twice with halogen, alkyl, $CF_3$, nitro and/or cyano; or R represents alkyl, alkenyl, alkynyl, cycloalkyl, cycloalkyl-alkyl, halo-alkyl, halo-alkenyl or halo-alkynyl; and $R^1$ and $R^2$, independently of each another, represent hydrogen, alkyl or alkoxy; or $R^1$ and $R^2$ together with the phosphor and the oxygen atoms to which they are bound form a heterocyclic (dioxaphospholane) ring.

In a most preferred embodiment the chemical compound of the invention is

[Bis-(4-fluorophenyl)-isopropoxy-methyl]-phosphonic acid dimethyl ester;

[(2-Fluorophenyl)-(4-fluorophenyl)-isobutoxy-methyl]-phosphonic acid dimethyl ester;

[(3-Fluorophenyl)-(4-fluorophenyl)-(4-nitro-3-trifluoromethyl-phenoxy)-methyl]-phosphonic acid dimethyl ester;

2-[Bis-(4-fluorophenyl)-isopropoxy-methyl]-[1,3,2]-dioxaphospholane 2-oxide;

[Cyclohexyl-(4-nitro-3-trifluoromethyl-phenyl)-(pyridin-2-yloxy)-methyl]-phosphonic acid dimethyl ester;

[Cyclohexyl-(4-fluorophenyl)-(4-nitro-3-trifluoromethyl-phenoxy)-methyl]-phosphonic acid dipropyl ester;

[(4-Chlorophenyl)-(4-fluorophenyl)-(4-nitro-3-trifluoromethyl-phenoxy)-methyl]-phosphonic acid dimethyl ester;

[1-(3,4-Dichlorophenoxy)-1-(4-fluorophenyl)-hexyl]-phosphonic acid dimethyl ester;

[1-(4-Fluorophenyl)-2-methyl-1-(4-nitro-3-trifluoromethyl-phenoxy)-propyl]-phosphonic acid dimethyl ester;

[(4-Fluorophenyl)-(6-fluoropyridin-2-yloxy)-(4-nitro-3-trifluoromethyl-phenyl)-methyl]-phosphonic acid dimethyl ester;

[(3,4-Dichlorophenyl)-(6-fluoropyridin-3-yloxy)-thiazol-2-yl-methyl]-phosphonic acid dimethyl ester; or

[(4-Fluorophenyl)-(1-methyl-1H-imidazol-2-yl)-(4-nitro-3-trifluoromethyl-phenoxy)-methyl]-phosphonic acid dimethyl ester;

an enantiomer or a mixture of enantiomers, or a pharmaceutically acceptable salt thereof, or an N-oxide thereof.

Any possible combination of two or more of the embodiments described herein is comprised within the scope of the present invention.

Definition of Substituents

In the context of this invention halogen represents a fluorine, a chlorine, a bromine or an iodine atom.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, tertiary pentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

In the context of this invention a haloalkyl group designates an alkyl group as defined herein, which alkyl group is substituted one or more times with halogen. Preferred haloalkyl groups of the invention include trihalogenmethyl.

In the context of this invention a hydroxy-alkyl group designates an alkyl group substituted with OH, wherein alkyl is as defined above.

In the context of this invention a cyano-alkyl group designates an alkyl group substituted with CN, wherein alkyl is as defined above.

In the context of this invention an alkenyl group designates a carbon chain containing one or more double bonds, including di-enes, tri-enes and poly-enes. In a preferred embodiment the alkenyl group of the invention comprises of from two to eight carbon atoms ($C_{2-8}$-alkenyl), more preferred of from two to six carbon atoms ($C_{2-6}$-alkenyl), including at least one double bond. In a most preferred embodiment the alkenyl group of the invention is ethenyl; 1- or 2-propenyl; 1-, 2- or 3-butenyl, 1,3-butdienyl; 1-, 2-, 3-, 4- or 5-hexenyl, or 1,3-hexdienyl, or 1,3,5-hextrienyl; 1-, 2-, 3-, 4-, 5-, 6-, or 7-octenyl, 1,3-octdienyl, 1,3,5-octtrienyl, or 1,3,5,7-octtetraenyl.

In the context of this invention a haloalkenyl group designates an alkenyl group as defined herein, which alkenyl group is substituted one or more times with halogen.

In the context of this invention an alkynyl group designates a carbon chain containing one or more triple bonds, including di-enes, tri-enes and poly-enes. In a preferred embodiment the alkynyl group of the invention comprises of from two to eight carbon atoms ($C_{2-8}$-alkynyl), more preferred of rom two to six carbon atoms ($C_{2-6}$-alkynyl), including at least one triple bond. In its most preferred embodiment the alkynyl group of the invention is ethynyl; 1-, or 2-propynyl; 1-, 2-, or 3-butynyl, 1,3-butdiynyl; 1-, 2-, 3-, 4-pentynyl, 1,3-pentdiynyl; 1-, 2-, 3-, 4-, or 5-henynyl, 1,3-hexdiynyl, 1,3,5-hextriynyl; 1-, 2-, 3-, 4-, 5- or 6-heptynyl, 1,3-heptdiynyl, 1,3,5-hepttriynyl; 1-, 2-, 3-, 4-, 5-, 6- or 7-octynyl, 1,3-octdiynyl, 1,3,5-octtriynyl, or 1,3,5,7-octtetraynyl.

In the context of this invention a haloalkynyl group designates an alkynyl group as defined herein, which alkynyl group is substituted one or more times with halogen.

In the context of this invention a cycloalkyl group designates a cyclic alkyl group, preferably containing of from three to seven carbon atoms ($C_{3-7}$-cycloalkyl), including cyclopropyl, cyclobutyl, cyclopentyl, cyclohexyl and cycloheptyl.

In the context of this invention a cycloalkyl-alkyl group designates a cycloalkyl group as defined above, which cycloalkyl group is substituted on an alkyl group as also defined above. Examples of preferred cycloalkyl-alkyl groups of the invention include cyclopropylmethyl and cyclopropylethyl.

In the context of this invention an alkoxy group designates an "alkyl-O—" group, wherein alkyl is as defined above. Examples of preferred alkoxy groups of the invention include methoxy and ethoxy.

In the context of this invention an alkoxy-alkyl group designates an "alkyl-O-alkyl-" group, and an alkoxy-alkoxy-alkyl group designates an "alkyl-O-alkyl-O-alkyl-" group, wherein alkyl is as defined above. Examples of preferred alkoxy-alkyl groups of the invention include methoxy-methyl, methoxy-ethyl, ethoxy-methyl, and ethoxy-ethyl, and examples of preferred alkoxy-alkoxy-alkyl groups of the invention include methoxy-methoxy-methyl, methoxy-methoxy-ethyl, methoxy-ethoxy-methyl, and methoxy-ethoxy-ethyl.

In the context of this invention an alkoxy-alkoxy group designates an "alkyl-O-alkyl-O—" group, wherein alkyl is as defined above. Examples of preferred alkoxy-alkoxy groups of the invention include methoxy-methoxy, methoxy-ethoxy, ethoxy-methoxy, and ethoxy-ethoxy.

In the context of this invention an alkoxy-alkoxy-akyl group designates an "alkyl-O-alkyl-O-alkyl-" group, wherein alkyl is as defined above. Examples of preferred alkoxy-alkoxy groups of the invention include methoxy-methoxy-methyl, methoxy-ethoxy-methyl, ethoxy-methoxy-methyl, ethoxy-ethoxy-methyl, methoxy-methoxy-ethyl, methoxy-ethoxy-ethyl, ethoxy-methoxy-ethyl, and ethoxy-ethoxy-ethyl.

In the context of this invention an acyl group designates a carboxy group (—COOH) or an alkyl-carbonyl group (alkyl-CO—), wherein alkyl is as defined above. Examples of preferred acyl groups of the invention include carboxy, acetyl, and propionyl.

In the context of this invention an alkoxy-carbonyl group designates an "alkyl-O—CO—" group, and an alkoxy-alkoxy-carbonyl group designates an "alkyl-O-alkyl-O—CO—" group, wherein alkyl is as defined above.

In the context of this invention an amino group may be a primary (—$NH_2$), secondary (—NH-alkyl), or tertiary (—N(alkyl)$_2$) amino group, i.e. it may be substituted once or twice with an alkyl group as defined above.

In the context of this invention a mono-, bi- or polycyclic carbocyclic group is a mono-, bi- or polycyclic compound, which holds only carbon atoms in its ring structure. The ring structures may in particular be aromatic (i.e. aryl) or partially or fully saturated.

In the context of this invention an aryl group designates a monocyclic or polycyclic aromatic hydrocarbon group. Examples of preferred aryl groups of the invention include phenyl, indenyl, naphthyl, azulenyl, fluorenyl, and anthracenyl.

In the context of this invention an aralkyl group designates an aryl group as defined above, which aryl group is attached to an alkyl group as also defined above. Examples of preferred aralkyl groups of the invention include benzyl.

In the context of this invention a mono-, bi- or polycyclic heterocyclic group is a mono-, bi- or polycyclic compound, which holds one or more heteroatoms in its ring structure. Preferred heteroatoms include nitrogen (N), oxygen (O), and sulphur (S). One or more of the ring structures may in particular be aromatic or partially saturated (i.e. a heteroaryl), or fully saturated.

Preferred monocyclic heteroaryl groups of the invention include aromatic 5- and 6 membered heterocyclic monocyclic groups, including furanyl, in particular 2- or 3-furanyl; thienyl, in particular 2 or 3-thienyl; pyrrolyl (azolyl), in particular 1,2 or 3-pyrrolyl; oxazolyl, in particular oxazol-2,4 or 5-yl; thiazolyl, in particular thiazol-2,4 or 5-yl; imidazolyl, in particular 1,2 or 4-imidazolyl; pyrazolyl, in particular 1,3 or 4-pyrazolyl; isoxazolyl, in particular isoxazol-3,4 or 5-yl; isothiazolyl, in particular isothiazol-3,4 or 5-yl; oxadiazolyl, in particular 1,2,3-, 1,2,4-, 1,2,5- or 1,3,4-oxadiazol-3,4 or 5-yl; triazolyl, in particular 1,2,3-, 1,2,4-, 2,1,3- or 4,1,2-triazolyl; thiadiazolyl, in particular thiadiazol-3,4 or 5-yl; pyridinyl, in particular 2,3 or 4-pyridinyl; pyridazinyl, in particular 3 or 4-pyridazinyl; pyrimidinyl, in particular 2,4 or 5-pyrimidinyl; pyrazinyl, in particular 2 or 3-pyrazinyl; and triazinyl, in particular 1,2,3-, 1,2,4- or 1,3,5-triazinyl.

Preferred bicyclic heteroaryl groups of the invention include indolizinyl, in particular 2,5 or 6-indolizinyl; indolyl, in particular 2,5 or 6-indolyl; isoindolyl, in particular 2,5 or 6-isoindolyl; benzo[b]furanyl, in particular 2,5 or 6-benzofuranyl; benzo[b]thienyl, in particular 2,5 or 6-benzothienyl; benzimidazolyl, in particular 2,5 or 6-benzimidazolyl; benzothiazolyl, in particular 5 or 6-benzothiazolyl; purinyl, in particular 2 or 8-purinyl; quinolinyl, in particular 2,3,6 or 7-quinolinyl; isoquinolinyl, in particular 3,6 or 7-isoquinolinyl; cinnolinyl, in particular 6 or 7-cinnolinyl; phthalazinyl, in particular 6 or 7-phthalazinyl; quinazolinyl, in particular 2,6 or 7-quinazolinyl; quinoxalinyl, in particular 2 or 6-quinoxalinyl; 1,8-naphthyridinyl, in particular 1,8-naphthyridin-2,3,6 or 7-yl; pteridinyl, in particular 2,6 or 7-pteridinyl; and indenyl, in particular 1,2,3,5 or 5-indenyl.

In the context of this invention a heteroaryl-alkyl group designates a mono-, bi- or poly-heterocyclic group as described above, which heterocyclic group is attached to an alkyl group as also defined above. Examples of preferred hetero-alkyl groups of the invention include furfuryl and picolyl.

In the context of this invention an N-oxide designates an oxide derivative of a nitrogen containing compound, e.g. N-containing heterocyclic compounds capable of forming such N-oxides.

Pharmaceutically Acceptable Salts

The chemical compound of the invention may be provided in any form suitable for the intended administration. Suitable forms include pharmaceutically (i.e. physiologically) acceptable salts, and pre- or prodrug forms of the chemical compound of the invention.

Examples of pharmaceutically acceptable addition salts include, without limitation, the non-toxic inorganic and organic acid addition salts such as the hydrochloride, the hydrobromide, the nitrate, the perchlorate, the phosphate, the sulphate, the formate, the acetate, the aconate, the ascorbate, the benzenesulphonate, the benzoate, the cinnamate, the citrate, the embonate, the enantate, the fumarate, the glutamate, the glycolate, the lactate, the maleate, the malonate, the mandelate, the methanesulphonate, the naphthalene-2-sulphonate derived, the phthalate, the salicylate, the sorbate, the stearate, the succinate, the tartrate, the toluene-p-sulphonate, and the like. Such salts may be formed by procedures well known and described in the art.

Metal salts of a chemical compound of the invention include alkali metal salts such as the sodium salt of a chemical compound of the invention containing a carboxy group.

Steric Isomers

The chemical compounds of the invention may exist in (+) and (−) forms as well as in racemic forms (±). The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphorsulphonate) salts for example.

The chemical compounds of the present invention may also be resolved by the formation of diastereomeric amides by reaction of the chemical compounds of the present invention with an optically active activated carboxylic acid such as that derived from (+) or (−) phenylalanine, (+) or (−) phenylglycine, (+) or (−) camphanic acid or by the formation of diastereomeric carbamates by reaction of the chemical compound of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Methods of Preparation

The chemical compounds of the invention may be prepared by conventional methods for chemical synthesis, e.g. those described in the working examples. The starting materials for the processes described in the present application are known or may readily be prepared by conventional methods from commercially available chemicals.

Also one compound of the invention can be converted to another compound of the invention using conventional methods.

The end products of the reactions described herein may be isolated by conventional techniques, e.g. by extraction, crystallisation, distillation, chromatography, etc.

Biological Activity

According to the present invention it has now been found that the chemical compounds of the invention possess valuable activity as modulators of $SK_{Ca}$ and/or $IK_{Ca}$ channels, in particular by having an inhibitory activity.

The SK/IK/BK channel modulating or inhibiting activity may be monitored using conventional electrophysiological methods such as patch-clamp techniques, or conventional spectroscopic methods such as FLIPR assay (Fluorescence Image Plate Reader; available from Molecular Devices). These methods generally comprises subjecting an $SK_{Ca}$ and/or $IK_{Ca}$ containing cell to the action of the chemical compound of the invention, followed by monitoring the membrane potential of the $SK_{Ca}$ and/or $IK_{Ca}$ containing cell in order to identify changes in the membrane potential caused by the action of the compound of the invention. Using such methods the chemical compounds of the invention show $IK_{Ca}$ inhibitory activity in concentrations below 100 μM, preferably below 10 μM, more preferred below 1 μm. In its most preferred embodiment compounds show $IK_{Ca}$ inhibitory activity show activity in low micromolar and the nanomolar range.

Based on their biological activity the compounds of the invention are considered useful for the for the treatment, prevention or alleviation of a disease or a disorder or a condition of a mammal, including a human, which disease, disorder or condition is responsive to modulation of $SK_{Ca}$ and/or $IK_{Ca}$ channels, including diseases or conditions like respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

The compounds of the invention are considered particularly useful for reducing or inhibiting undesired immune-regulatory actions. In a preferred embodiment, therefore, the compounds of the may be used in the treatment or alleviation of a diseases, disorders or condition related to immune dysfunction, or in order to obtain immune suppression in an individual in need therefore.

In a more preferred embodiment, the invention relates to the use of an $IK_{Ca}$ inhibitory compound of the invention in a combination therapy with known immune-suppressants for the treatment or alleviation of a diseases, disorders or condition related to immune dysfunction, or for obtaining immune suppression. Preferred immune-suppressants to combine with the compounds of the invention include Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, and the calcineurin inhibitors (protein phosphatase 2B inhibitors), in particular Cyclosporin.

Conditions which may benefit from this treatment include, but are not limited to diseases, disorders or conditions such as auto-immune diseases, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, auto-immune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

Pharmaceutical Compositions

In another aspect the invention provides novel pharmaceutical compositions comprising a therapeutically effective amount of the chemical compound of the invention.

While a chemical compound of the invention for use in therapy may be administered in the form of the raw chemical compound, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the chemical compound of the invention, or a pharmaceutically acceptable salt or derivative thereof, together with one or more pharmaceutically acceptable carriers therefore, and, optionally, other therapeutic and/or prophylactic ingredients, know and used in the art. The carrier(s) must be "acceptable" in the sense of being compatible with the other ingredients of the formulation and not harmful to the recipient thereof.

The pharmaceutical composition of the invention may be administered by any convenient route, which suits the desired therapy. Preferred routes of administration include oral administration, in particular in tablet, in capsule, in dragé, in powder, or in liquid form, and parenteral administration, in particular cutaneous, subcutaneous, intramuscular, or intravenous injection. The pharmaceutical composition of the invention can be manufactured by any skilled person by use of standard methods and conventional techniques appropriate to the desired formulation. When desired, compositions adapted to give sustained release of the active ingredient may be employed.

Further details on techniques for formulation and administration may be found in the latest edition of *Remington's Pharmaceutical Sciences* (Maack Publishing Co., Easton, Pa.).

The actual dosage depend on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 μg/kg i.v. and 1 μg/kg p.o. The upper limit of the dosage range is presently considered to be about 10 mg/kg i.v. and 100 mg/kg p.o. Preferred ranges are from about 0.1 μg/kg to about 10 mg/kg/day i.v., and from about 1 μg/kg to about 100 mg/kg/day p.o.

Methods of Therapy

In another aspect the invention provides a method for the treatment, prevention or alleviation of a disease or a disorder or a condition of a living animal body, including a human, which disease, disorder or condition is responsive to inhibition of $SK_{Ca}$ and/or $IK_{Ca}$ channels, and which method comprises administering to such a living animal body, including a human, in need thereof an effective amount of a chemical compound of the invention.

In a more preferred embodiment the disease or a disorder or a condition is a respiratory diseases such as asthma, cystic fibrosis, chronic obstructive pulmonary disease and rhinorrhea, convulsions, vascular spasms, coronary artery spasms, renal disorders, polycystic kidney disease, bladder spasms, urinary incontinence, bladder outflow obstruction, irritable bowel syndrome, gastrointestinal dysfunction, secretory diarrhoea, ischaemia, cerebral ischaemia, ischaemic hearth disease, angina pectoris, coronary hearth disease, traumatic brain injury, psychosis, anxiety, depression, dementia, memory and attention deficits, Alzheimer's disease, dysmenorrhea, narcolepsy, Reynaud's disease, intermittent claudication, Sjorgren's syndrome, migraine, arrhythmia, hypertension, absence seizures, myotonic muscle dystrophia, xerostomi, diabetes type II, hyperinsulinemia, premature labour, baldness, cancer, and immune suppression.

In an even more preferred embodiment, the disease, disorder or condition relates to reduction or inhibition of undesired immune-regulatory actions, including graft vs. host syndrome, transplant rejection, or transplant rejection. In a further preferred embodiment this method comprises simultaneous administration of a pharmaceutically effective amount of a conventional immune suppressing agent. Conventional immune-suppressing agent for use according to the invention include Amphotericin, Busulphan, Co-trimoxazole, Chlorambucil, colony stimulating factors, corticosteroids, Cyclophosphamide, Fluconazole, folinic acid, Ganciclovir, antilymphocyte immunoglobulins, normal immunoglobulins, Methotrexate, Methylprednisolone, Octreotide, Oxpentifylline, Tacrolimus (FK506), Thalidomide, Zolimomab aritox, or the calcineurin inhibitors (protein phosphatase 2B inhibitors), in particular Cyclosporin.

Conditions which may benefit from this treatment include, but are not limited to diseases, disorders or conditions such as auto-immune diseases, e.g. Addison's disease, alopecia areata, Ankylosing spondylitis, haemolytic anemia (anemia haemolytica), pernicious anemia (anemia perniciosa), aphthae, aphthous stomatitis, arthritis, arteriosclerotic disorders, osteoarthritis, rheumatoid arthritis, aspermiogenese, asthma bronchiale, auto-immune asthma, auto-immune hemolysis, Bechet's disease, Boeck's disease, inflammatory bowel disease, Burkitt's lymphoma, Chron's disease, chorioiditis, colitis ulcerosa, Coeliac disease, cryoglobulinemia, dermatitis herpetiformis, dermatomyositis, insulin-dependent type I diabetes, juvenile diabetes, idiopathic diabetes insipidus, insulin-dependent diabetes mellisis, auto-immune demyelinating diseases, Dupuytren's contracture, encephalomyelitis, encephalomyelitis allergica, endophthalmia phacoanaphylactica, enteritis allergica, auto-immune enteropathy syndrome, erythema nodosum leprosum, idiopathic facial paralysis, chronic fatigue syndrome, febris rheumatica, glomerulo nephritis, Goodpasture's syndrome, Graves' disease, Hamman-Rich's disease, Hashimoto's disease, Hashimoto's thyroiditis, sudden hearing loss, sensoneural hearing loss, hepatitis chronica, Hodgkin's disease, haemoglobinuria paroxysmatica, hypogonadism, ileitis regionalis, iritis, leucopenia, leucemia, lupus erythematosus disseminatus, systemic lupus erythematosus, cutaneous lupus erythematosus, lymphogranuloma malignum, mononucleosis infectiosa, myasthenia gravis, traverse myelitis, primary idiopathic myxedema, nephrosis, ophthalmia symphatica, orchitis granulomatosa, pancreatitis, pemphigus, pemphigus vulgaris, polyarteritis nodosa, polyarthritis chronica primaria, polymyositis, polyradiculitis acuta, psoreasis, purpura, pyoderma gangrenosum, Quervain's thyreoiditis, Reiter's syndrome, sarcoidosis, ataxic sclerosis, progressive systemic sclerosis, scleritis, sclerodermia, multiple sclerosis, sclerosis disseminata, acquired spenic atrophy, infertility due to antispermatozoan antobodies, thrombocytopenia, idiopathic thrombocytopenia purpura, thymoma, acute anterior uveitis, vitiligo, AIDS, HIV, SCID and Epstein Barr virus associated diseases such as Sjorgren's syndrome, virus (AIDS or EBV) associated B cell lymphoma, parasitic diseases such as Lesihmania, and immunosuppressed disease states such as viral infections following allograft transplantations, graft vs. Host syndrome, transplant rejection, or AIDS, cancers, chronic active hepatitis diabetes, toxic chock syndrome, food poisoning, and transplant rejection.

It is at present contemplated that a suitable dosage of the active pharmaceutical ingredient (API) is within the range of from about 0.1 to about 1000 mg API per day, more preferred of from about 10 to about 500 mg API per day, most preferred of from about 30 to about 100 mg API per day, dependent, however, upon the exact mode of administration, the form in which it is administered, the indication considered, the subject and in particular the body weight of the subject involved, and further the preference and experience of the physician or veterinarian in charge.

EXAMPLES

The invention is further illustrated with reference to the following examples, which are not intended to be in any way limiting to the scope of the invention as claimed. These examples demonstrate general methods for the synthesis of the preferred compounds in this invention, and some preferred methods for synthesis of certain embodied compounds.

2-[Bis-(4-fluoro-phenyl)-(4-nitro-3-trifluoromethyl-phenoxy)-methyl]-thiazole (Compound 1)

A solution of thiazole (2.6 g) in THF (20 ml) at −78° C. under nitrogen was treated with 2.5M n-BuLi (12.25 ml) over 15 min. After stirring for 30 min a solution of p-fluorobenzophenone (6.54 g) in THF (20 ml) was added and stirring continued overnight with gradual warming to room temperature. The reaction was quenched with sat. aq. NH$_4$Cl and extracted with ethyl ether (3×). Drying (MgSO$_4$), filtration and concentration afforded the carbinol as a solid (8.5 g, m.p.=88.6–89.5° C.). This material (0.5 g) was dissolved in DMF (5 ml) and treated with NaH (60% dispersion in paraffin, 76 mg). After stirring for 45 min at room temperature 5-fluoro-2-nitrobenzotrifluoride (0.44 g) was added and the reaction heated to 60° C. After 5 days the reaction was quenched with sat. aq. NH$_4$Cl and extracted with ethyl ether (3×). Drying of the combined organic layers (MgSO$_4$), filtration, concentration and flash chromatography afforded the title compound (9%; M.p. 133–134° C.).

2-[(2-Fluoro-phenyl)-bis-(4-fluoro-phenyl)-methoxy]-[1,3,2]-dioxaphospholane (Compound 2)

o-Fluorophenyl-di-p-fluorophenylmethanol (628 mg) dissolved in dry toluene (10 ml) was treated with 2-chloro-1,3,2-dioxaphospholane (292 mg) and refluxed for 10 hrs. The toluene was evaporated and the crude residue was purified by flash column chromatography to afford 260 mg of the title compound (32%; M.p. 163–164° C.).

2-[Tris-(4-fluoro-phenyl)-methoxy]-[1,3,2]-dioxaphospholane (Compound 3) was prepared in similar fashion in 14% yield, m.p. 195–196° C.

2-(2-Fluoro-phenyl)-2-(4-fluoro-phenyl)-pent-4-enenitrile (Compound 4)

o-Fluorophenyl-p-fluorophenylacetonitrile (1.0 g) was dissolved in dry DME (5 ml) and treated with NaH (60% dispersion in paraffin, 190 mg). After stirring for 30–45 min. at room temperature allyl bromide (0.8 g) was added and stirring continued overnight. The reaction was quenched with sat. aq. NH$_4$Cl and extracted with ethyl acetate (3×). Drying of the combined organic layers (MgSO$_4$), filtration, concentration and flash chromatography afforded the title compound (39%; M.p. 215–219° C.).

2-(2-Fluoro-phenyl)-2-(4-fluoro-phenyl)-3-methyl-butyronitrile (Compound 5) was prepared in similar fashion in 47% yield, isolated as an oil.

2,2-Bis-(4-fluoro-phenyl)-3-methyl-butyronitrile (Compound 6) was prepared in similar fashion in 52% yield, isolated as an oil.

2,2-Bis-(4-fluoro-phenyl)-4-methyl-pentanenitrile (Compound 7) was prepared in similar fashion in 65% yield, isolated as an oil.

2,2-Bis-(4-fluoro-phenyl)-pent-4-enenitrile (Compound 8) was prepared in similar fashion in 70% yield, isolated as an oil.

2,2-Bis-(4-fluoro-phenyl)-pent-4-ynenitrile (Compound 9) was prepared in similar fashion in 62% yield, m.p. 59.7–60.5° C.

2-(2-Fluoro-phenyl)-2-(4-fluoro-phenyl)-pent-4-ynenitrile (Compound 10) was prepared in similar fashion in 33% yield, isolated as an oil.

2-(2-Fluoro-phenyl)-2-(4-fluoro-phenyl)-4-methyl-pentanenitrile (Compound 11) was prepared in similar fashion in 79% yield, isolated as an oil.

2,2-Bis-(4-fluoro-phenyl)-3,3-diphenyl-propionitrile (Compound 12) was prepared in similar fashion in 84% yield, m.p. 208–212.5° C.

2-(2-Fluoro-phenyl)-2-(4-fluoro-phenyl)-3,3-diphenyl-propionitrile (Compound 13) was prepared in similar fashion in 76% yield, m.p. 210–215.3° C.

2-(3-Fluoro-phenyl)-2-(4-fluoro-phenyl)-3-methyl-butyronitrile (Compound 14) was prepared in similar fashion in 65% yield, isolated as an oil.

2-(3-Fluoro-phenyl)-2-(4-fluoro-phenyl)-4-methyl-pentanenitrile (Compound 15) was prepared in similar fashion in 51% yield, isolated as an oil.

2-(3-Fluoro-phenyl)-2-(4-fluoro-phenyl)-pent-4-enenitrile (Compound 16) was prepared in similar fashion in 72% yield, isolated as an oil.

2-(3-Fluoro-phenyl)-2-(4-fluoro-phenyl)-pent-4-ynenitrile (Compound 17) was prepared in similar fashion in 73% yield, isolated as an oil.

2,2-Bis-(4-fluoro-phenyl)-3-oxo-butyronitrile (Compound 18) was prepared in similar fashion in 38% yield, m.p. <50° C.

2,2-Bis-(4-fluoro-phenyl)-3-methyl-butyramide (Compound 19)

2,2-Bis-(4-fluoro-phenyl)-3-methyl-butyronitrile (2.21 g) was suspended in acetic acid (2 ml) and conc. sulphuric acid (2 ml) and heated to 130° C. for 1.5 hrs. The reaction mixture was poured onto ice/water and the pH adjusted to 9 with aq. ammonium hydroxide. The mixture was extracted with dichloromethane (3×), washed with water (2×) and brine, dried (MgSO$_4$), filtered and concentrated. The product was taken up in dichloromethane and triturated with cold hexane to precipitate the title compound (50%; M.p. 142.3–147.0° C.).

3-Ethoxy-2-(4-fluoro-phenyl)-2-(2-fluoro-phenyl)-propionitrile (Compound 20)

A solution of o-fluorophenyl-p-fluorophenylacetonitrile (1.7 g) in THF (10 ml) was treated with sodium hydride (60% dispersion in paraffin) (0.2 g) under Argon. To the formed suspension, chloromethyl ethyl ether (0.8 g) was added dropwise and the reaction mixture was stirred at room temperature overnight. The mixture was filtered and concentrated. Flash chromatography of the residue afforded the title compound (1.1 g; Isolated as an oil).

3-Ethoxy-2,2-bis-(4-fluoro-phenyl)-propionitrile (Compound 21) was prepared in similar fashion in 80% yield from di-p-fluorophenylacetonitrile and chloromethyl ethyl ether, isolated as an oil.

Cyano-(4-fluoro-phenyl)-(2-fluoro-phenyl)-acetic acid methyl ester (Compound 22) was prepared in similar fashion in 23% yield from o-fluorophenyl-p-fluorophenylacetonitrile and methyl chloroformate, m.p. 104–105° C.

2,2-Bis-(4-fluoro-phenyl)-3-(2-methoxy-ethoxy)-propionitrile (Compound 23) was prepared in similar fashion in 70% yield from di-p-fluorophenylacetonitrile and MEM-chloride, isolated as an oil.

2,2-Bis-(4-fluoro-phenyl)-succinonitrile (Compound 24) was prepared in similar fashion in 38% yield from di-p-fluorophenylacetonitrile and chloroacetonitrile, m.p. 93–94° C.

3-Cyano-3-(4-fluoro-phenyl)-3-(2-fluoro-phenyl)-propionic acid ethyl ester (Compound 25)

A solution of o-fluorophenyl-p-fluorophenylacetonitrile (1.7 g) in ethylmethyl ketone (10 ml) was treated with potassium carbonate (2 g) and potassium iodide (0.1 g). To the formed suspension, ethyl bromoacetate (2 g) was added dropwise and the reaction mixture was refluxed overnight. The mixture was filtered and concentrated. Flash chromatography of the residue afforded the title compound (1.4 g; Viscous gum).

3-Cyano-3,3-bis-(4-fluoro-phenyl)-propionic acid ethyl ester (Compound 26) was prepared in similar fashion in 61% yield using di-p-fluorophenylacetonitrile and ethyl bromoacetate, isolated as an oil.

2-[Cyano-bis-(4-fluoro-phenyl)-methyl]-malonic acid diethyl ester (Compound 27)

To THF (80 ml) were added sequentially, a 1.0 M solution of TiCl$_4$ in dichloromethane (80 ml), p,p'-difluorobenzophenone (8.73 g) and diethtyl malonate (6.4 g) in THF 20 ml. After stirring at 0° C. for 40 min, a solution of pyridine (12.8 ml) in THF (28 ml) was added dropwise. The ensuing mixture was stirred for 4 days. The reaction was quenched with water and diethyl ether. The aqueous phase was separated and extracted twice more with diethyl ether. The combined organic phases were washed with brine, sat. sodium bicarbonate solution and again with brine. Drying of the organic phase (MgSO$_4$), filtration and concentration afforded a residue from which residual diethyl malonate was removed by Kugelrohr destillation. The residue was flash chromatographed to provide 1,1-di-p-fluorophenyl-2,2-diethoxycarbonylethylene (25%, m.p.=117–119° C.). To this product (5.9 g) were added ammonium chloride (1.31 g), KCN (2.18 g), DMF (175 ml) and water (22 ml) and the mixture was heated to 100° C. for 8 hrs. The cooled reaction mixture was poured into water and extracted (3×) with ethyl ether. The combined organic phases were washed with water, aq. 2N HCl, aq. 5% NaHCO₃ and brine. Drying (Na₂SO₄), filtration and evaporation of volatiles gave a residue which was recrystallised from ether-hexane to afford the title compound (56%; M.p. 90–91° C.).

2,2-Bis-(4-fluoro-phenyl)-4-hydroxy-butyronitrile (Compound 28)

Ethylene glycol dimethyl ether (10 ml) was treated with sodium borohydride (142 mg) and LiCl (228 mg) and the mixture stirred for 30 min. 3-Cyano-3,3-bis-(4-fluoro-phenyl)-propionic acid ethyl ester (847 mg) was added and the mixture stirred for 6 hrs, before more sodium borohydride (36 mg) and LiCl (57 mg) were added and stirring continued overnight. The mixture was poured into water and extracted (3×) with ethyl ether. The combined organic extracts were dried over Na₂SO₄. Filtration, concentration and flash chromatography of the residue afforded the title compound (41%; Isolated as an oil).

1

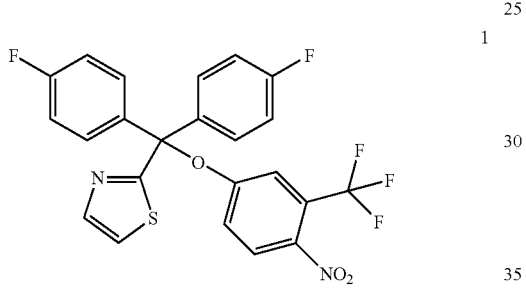

2

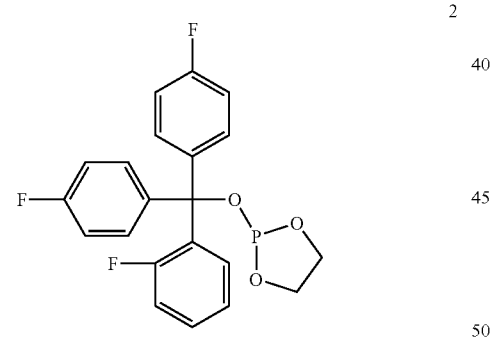

3

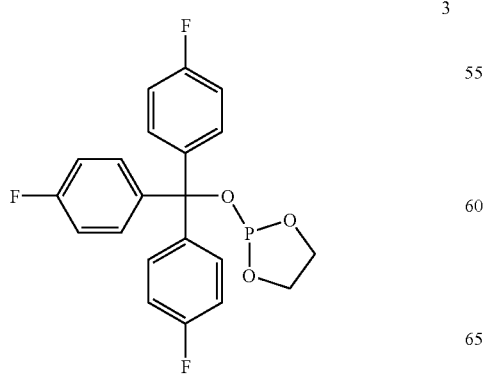

-continued

4

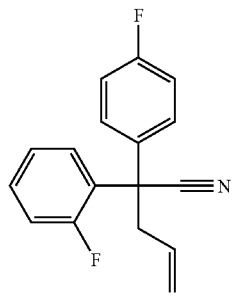

5

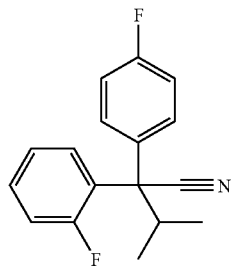

6

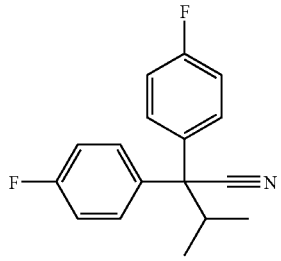

7

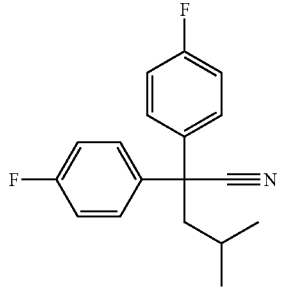

8

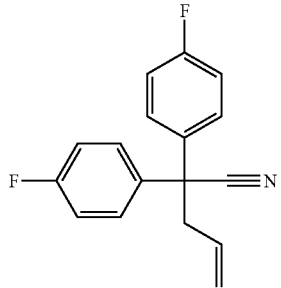

9
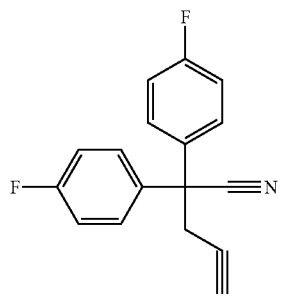
10
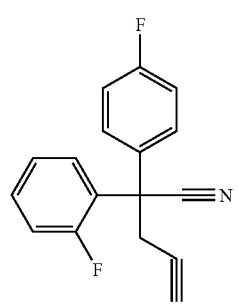
11
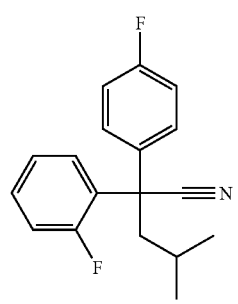
12
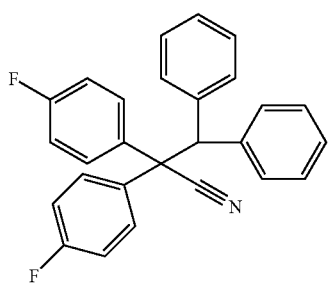
13
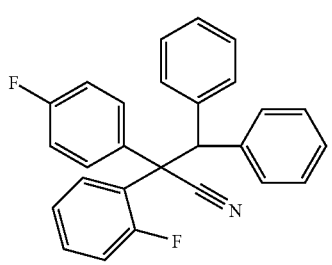
14
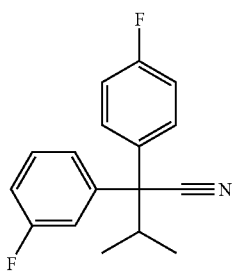
15
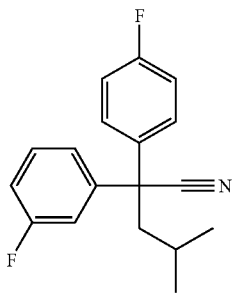
16
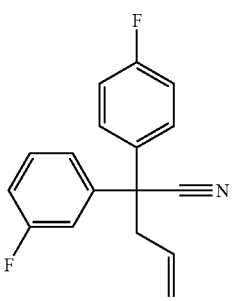
17
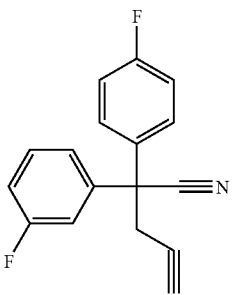
18
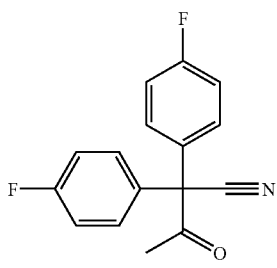

-continued
19
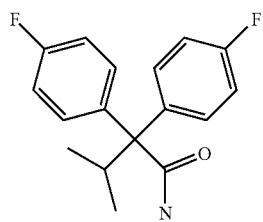
20
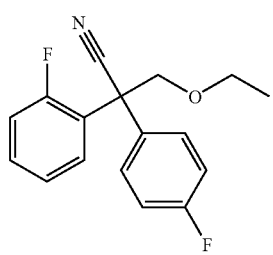
21
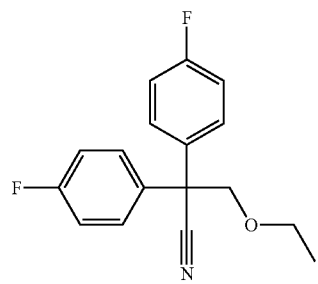
22
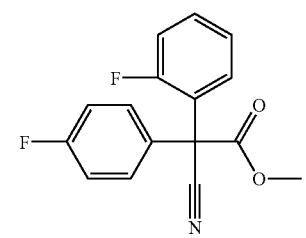
23
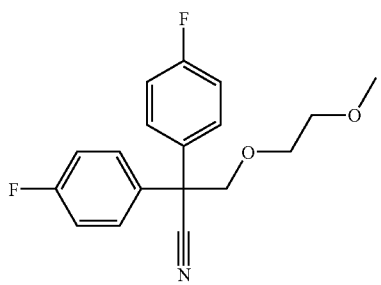
24
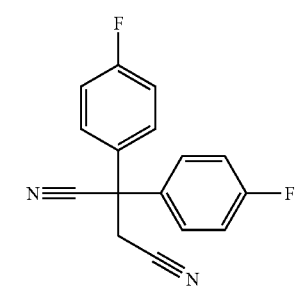
-continued
25
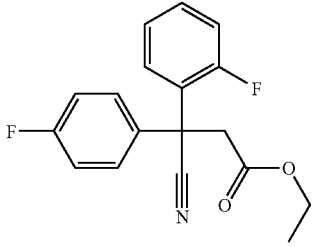
26
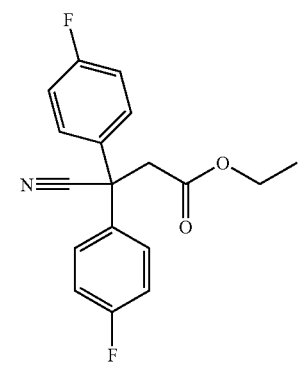
27
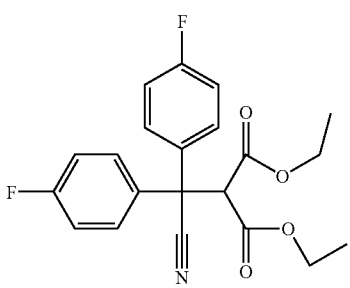
28
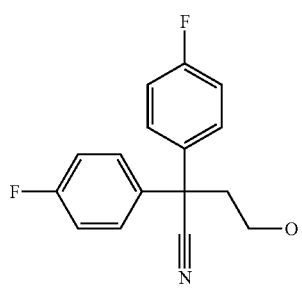

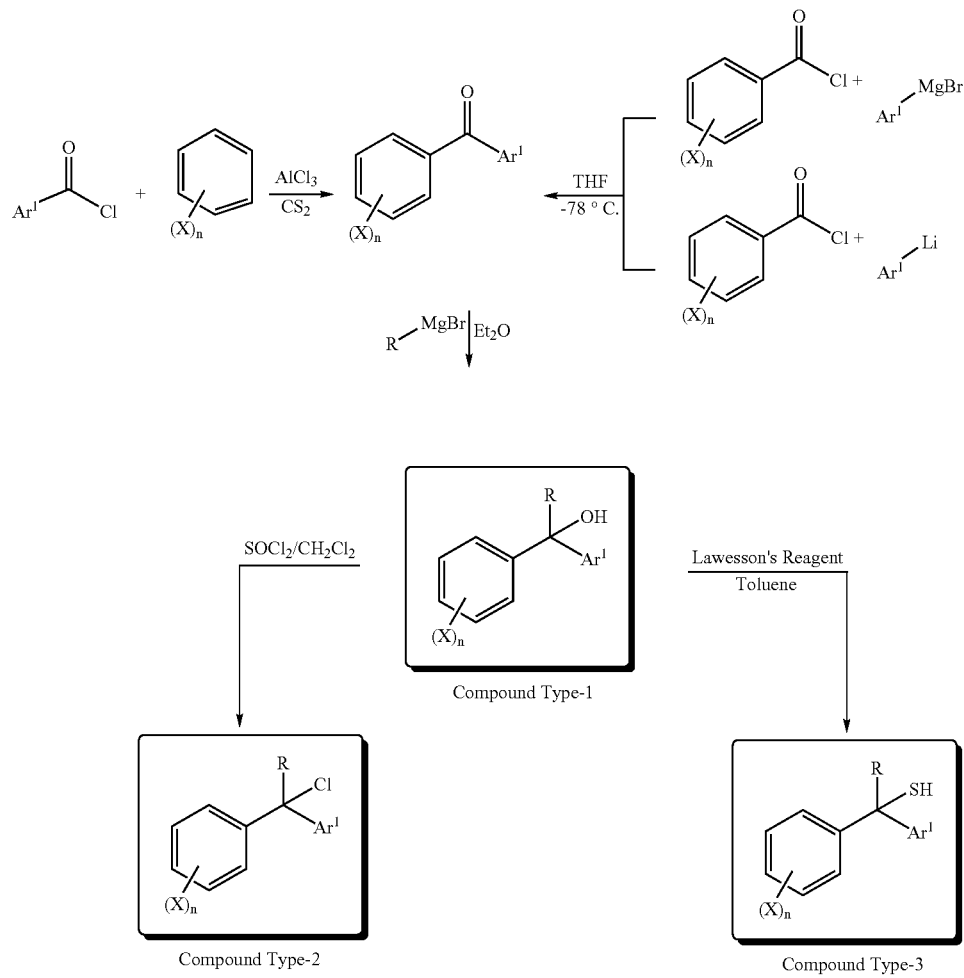

Compound Type-1

Compound Type-2

Compound Type-3

General Method for the Preparation of Compound Type 1 Synthesis of Tri Substituted Methanole:

A solution of a substituted benzene (2.5 equivalent) and aluminum chloride (5 equivalent) in dry carbon disulfide (0.5 L/mol) is heated to gentle reflux. An arylcarbonylchloride (2 equivalent) is added slowly from a dropping funnel. After 1 hour the addition is completed and the gentle reflux is continued for another hour. The dropping funnel is removed, a condenser is attached and carbon disulfide is distilled. The reaction mixture is poured slowly over a mixture of cracked ice and hydrochloric acid. The aqueous phase is extracted twice with toluene, the extract are combined and washed with water, aqueous sodium hydroxide and dried over sodium sulfate. Evaporation of the solvent gave the phenyl-aryl ketone in 69–90% yield.

The substituted phenyl-aryl ketone is added drop-wise to a refluxing solution of a Grignard Reagents in ether. After 3 hours the reaction mixture is cooled and poured into water. The aqueous phase is extracted twice with methylene chloride and the combined organic phases is dried with sodium sulfate, filtrated and the solvent evaporated. The crude product are crystallized or purified by column chromatography to give trisubstitutedmethanoles in 73–90% yield.

General Method for the Preparation of Compound Type 2 Synthesis of Tri Substituted Chloromethane:

A solution of a compound Type 1 in methylene chloride (2 mL/mmol) is heated to gentle reflux. Thionylchloride (2 equivalent) is added from a dropping funnel during 15 minutes and the reflux is continued for another 1 hour. Excess thionylchloride and methylene chloride is removed by evaporation. Toluene is added twice, and evaporated to afford crude tri substituted chloromethane in 95–100% yield. This product was used without purification in the next step.

General Method for the Preparation of Compound Type 3 Synthesis of Tri Substituted Methyl Mercaptane:

A solution of a compound Type 1 in toluene is heated to gentle reflux with 2,4-bis(p-methoxyphenyl)-1,3-dithia-phosphetane-2,4-disulphide for 1 hour. Toluene is removed by evaporation and the crude product is purified by column chromatography affording tri substituted methyl mercaptane in 90–100% yield.

General Method for the Preparation of Compound Type 4 Synthesis of Tri Substituted Methyl Carbamates

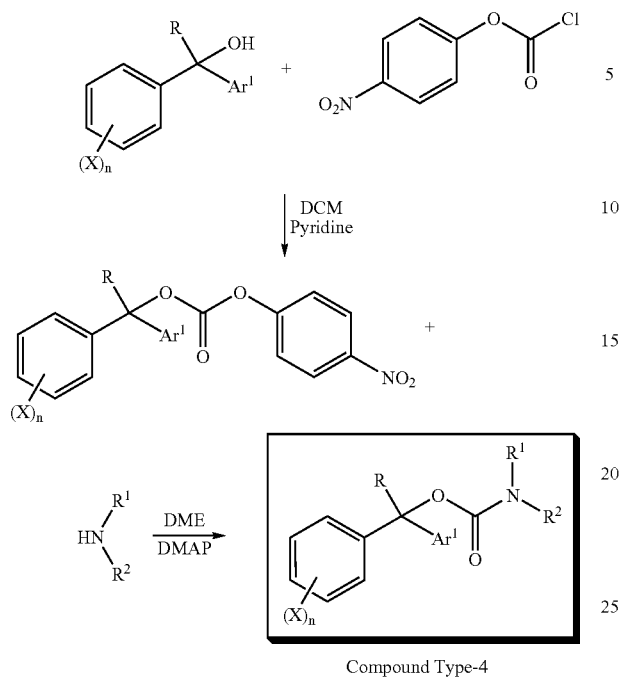

Compound Type-4

A compound Type 1 is dissolved in dichloromethane (DCM) (3 mL/mmol), pyridine (1 equivalent) and 4-nitrophenyl chloroformate (1 equivalent) are added and the solution is heated to refluxed for 3 hour. The reaction mixture is cooled washed with aq hydrochloric acid, 10% sodium carbonate and water. Dried with magnesium sulfate, filtrated and the solvent removed under reduced pressure. The crude product is purified by column chromatography affording substituted carbonate in 77–86% yield.

The substituted carbonate is dissolved in dimethoxyethane (DME) (3 mL/mmol), and the amine is added (1 equivalent) together with 4-dimethylaminopyridine (DMAP) (1 equivalent). The reaction mixture is heated for 14 hours at 50° C., cooled to room temperature, washed with aq hydrochloric acid, 10% sodium carbonate and water. Dried with magnesium sulfate, filtrated and the solvent removed under reduced pressure. The crude product is purified by column chromatography affording substituted carbamate in 74–80% yield.

In this way the following tri substituted methyl carbamates are obtained:

(±)-Carbamic acid tris-(4-fluorophenyl)-methyl ester (Compound 4-1);

(±)-Carbamic acid cyclohexyl-bis-(4-fluorophenyl)-methyl ester (Compound 4-2);

(±)-Carbamic acid cyclohexyl-(4-fluorophenyl)-thiazol-2-yl-methyl ester (Compound 4-3);

(±)-Piperidine-1-carboxylic acid tris-(4-fluorophenyl)-thiazol-2-yl-methyl ester (Compound 4-4);

(±)-Methyl-carbamic acid cyclopentyl-bis-(4-fluorophenyl)-methyl ester (Compound 4-5);

(±)-Pyrrolidine-1-carboxylic acid cyclohexyl-bis-(4-fluorophenyl)-methyl ester (Compound 4-6);

(±)Methyl-carbamic acid tris-(4-fluorophenyl)-methyl ester (Compound 4-7);

(±)-Methyl-carbamic acid cyclohexyl-(2-fluorophenyl)-(4-fluorophenyl)-methyl ester (Compound 4-8);

(±)-Carbamic acid cyclohexyl-(4-fluorophenyl)-pyridin-2-yl-methyl ester (Compound 4-9);

(±)-Dimethyl-carbamic acid tris-(4-fluorophenyl)-methyl ester (Compound 4-10);

(±)-Carbamic acid (2-fluorophenyl)-bis-(4-fluorophenyl)-methyl ester (Compound 4-11); and (±)-Carbamic acid (2-fluorophenyl)-(4-fluorophenyl)-phenyl-methyl ester (Compound 4-12).

4-1

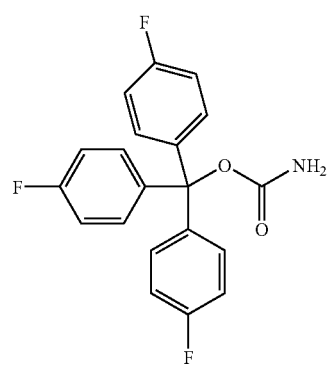

4-2

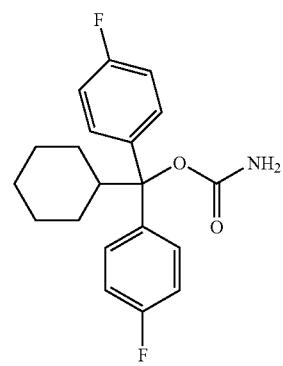

4-3

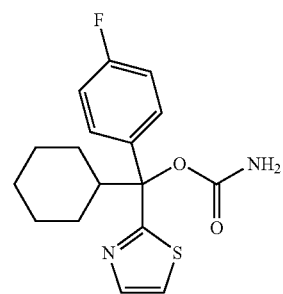

4-4

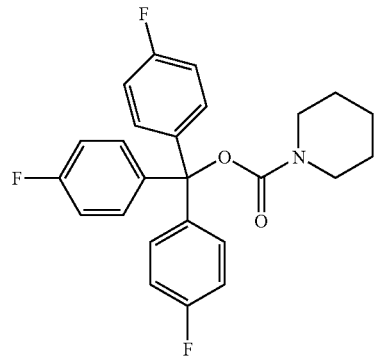

-continued
4-5
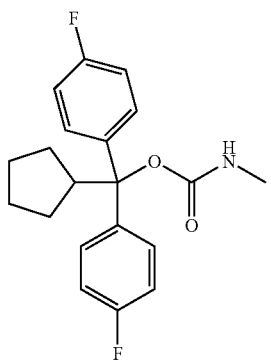
4-6
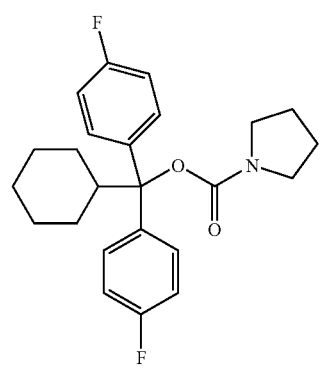
4-7
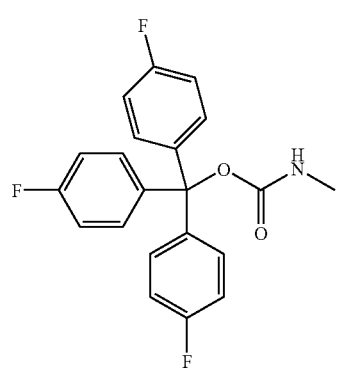
4-8
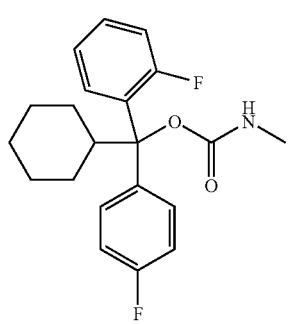
-continued
4-9
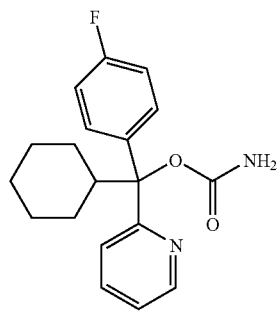
4-10
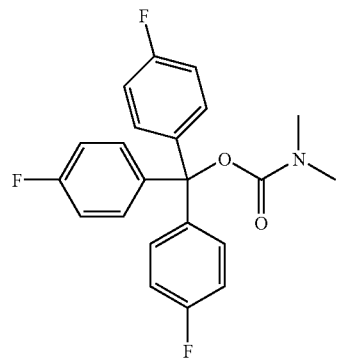
4-11
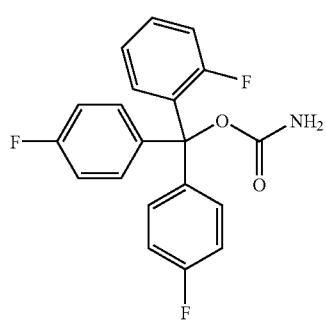
4-12
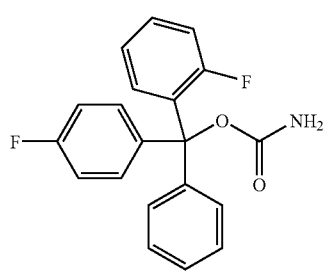
General Method for the Preparation of Compound Type 5
Synthesis of Tri Substituted Methyl Sulfide

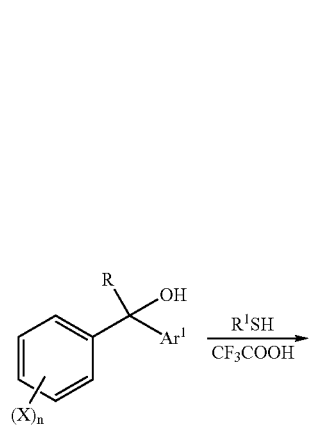
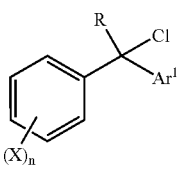
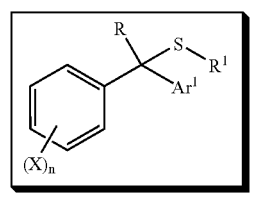

Compound Type-5

Magnesium tunings in anhydrous diethyl ether is heated to gentle reflux, and a solution of compound Type 2 (1 equivalent) in anhydrous diethyl ether is added slowly from a dropping funnel at such a rate that gentle reflux continue without further heating. When the addition is completed, the reaction mixture is heated to gentle reflux until only traces of unreacted magnesium remains. The reaction mixture is cooled in an ice bath, and finely powered sulfur (1 equivalent) is added and the reaction is heated to gentle reflux for another 1 hour. (OBS! A vigorous reaction with sulfur takes place when the reaction is heated for reflux).

The reaction mixtures is cooled again on the ice bath, alkyl bromide (1.1 equivalent) is added dropwise from the funnel, and the mixture is heated for reflux 16 hours then cooled. DCM is added and the reaction mixture is washed twice with 5% sodium hydroxide and twice with water. Dried with magnesium sulfate, filtrated and the solvent removed under reduced pressure. The crude product is purified by column chromatography (hexane:DCM) affording sulfide Type 5 in 60–84% yield.

In this way the following tri substituted methyl sulfides are obtained:

2-[Cyclohexyl-(4-fluorophenyl)-(2-fluorophenyl)-methylsulfanyl]-thiazole (Compound 5-1);

2-[(2-Chlorophenyl)-cyclohexyl-(4-fluorophenyl)-(2-fluorophenyl)-methylsulfanyl]-1-methyl-1H-imidazole (Compound 5-2);

2-[(4-Chlorophenylsulfanyl)-cyclopentyl-(4-fluorophenyl)-(2-fluorophenyl)-methyl]-pyridine (Compound 5-3);

2-[Cyclohexyl-(3,4-dichlorophenyl)-(1H-imidazol-2-yl)-methylsulfanyl]-pyridine (Compound 5-4);

2-[Cyclopentyl-(2-fluorothiazol-4-yl )-(4-nitro-3-trifluoromethylphenyl)-methylsulfanyl]-pyridine (Compound 5-5);

2-[(4-fluorophenyl)-(4-fluorophenylsulfanyl)-(4-nitro-3-trifluoromethylphenyl)-methyl]-thiazole (Compound 5-6);

2-[Cyclohexylsulfanyl-(4-fluorophenyl)-(4-nitro-3-trifluoromethylphenyl)-methyl]-thiazole (Compound 5-7);

2-[Cyclopentylsulfanyl-bis-(4-fluorophenyl)-methyl]-1-methyl-1H-imidazole (Compound 5-8);

4-[Cyclohexylsulfanyl-bis-(4-fluorophenyl)-methyl]-2-fluoro-thiazole (Compound 5-9);

2-[Bis-(4-fluorophenyl)-(2-fluorophenyl)-methylsulfonyl]-thiazole (Compound 5-10);

1-Methyl-2-[tris-(4-fluorophenyl)-methylsulfanyl]-1H-imidazole (Compound 5-11); Mp. 135.5–140.5° C.;

2-[Tris-(4-fluorophenyl)-methylsulfanyl]-pyridine (Compound 5-12); isolated as an oil; and 2-[Tris-(4-fluorophenyl)-methylsulfanyl]-pyridine-N-oxide (Compound 5-13); Mp. 147.7–151.8° C.

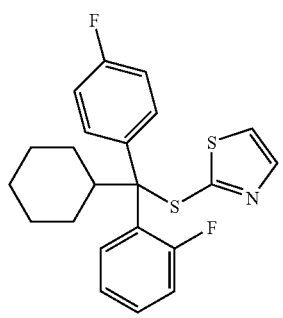

5-1

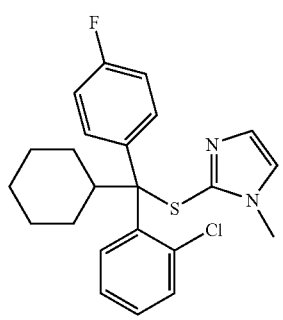

5-2

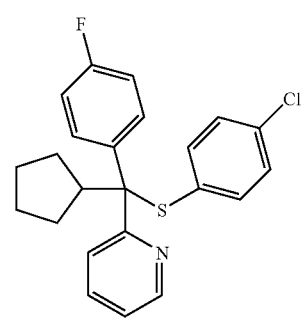

5-3

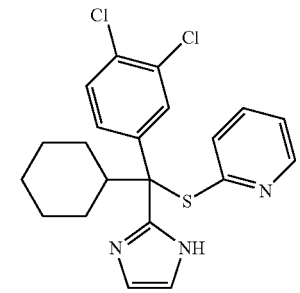

5-4

-continued
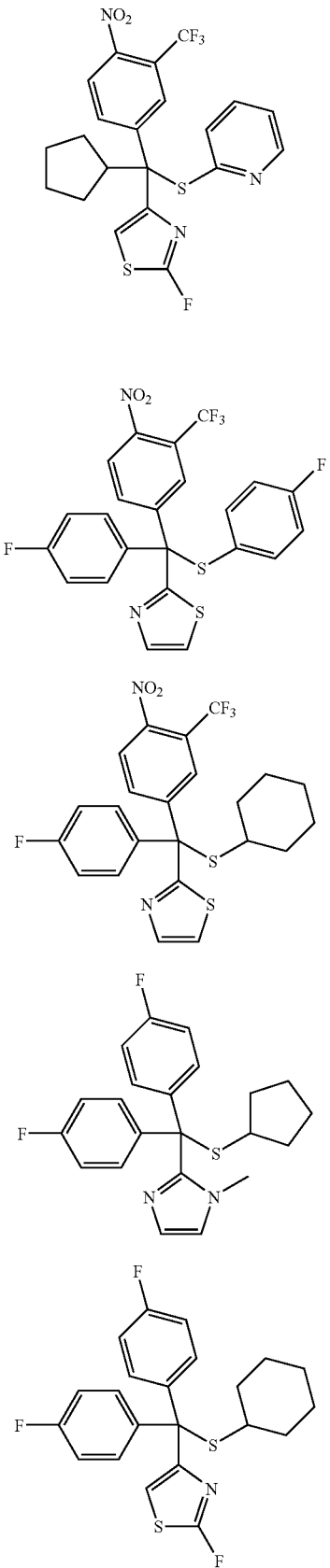
5-5
5-6
5-7
5-8
5-9
-continued
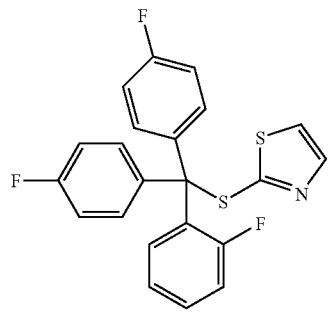
5-10
5-11
5-12
5-13
2-[Bis-(4-fluoro-phenyl)-(2-fluoro-phenyl)-methyl-sulfanyl]-N,N-diethyl-acetamide (Compound 5-14)
Metallic sodium (1 mmol) was dissolved in dry methanol (8 ml) and o-fluorophenyl-di-p-fluorophenylmethyl sulfide (0.91 mmol) was added at room temperature under Argon. After stirring for 15 min, N,N-diethyl chloroacetamide (1 mmol) was added dropwise. After stirring for another hour at room temperature the reaction mixture was poured into water. Extraction with diethyl ether (3×), drying with sodium sulfate, filtration and concentration gave a residue, which was flash-chromatographed to afford the title compound as a white solid (52%; M.p. 122–123° C.).

2-[Bis-(4-fluoro-phenyl)-(2-fluoro-phenyl)-methylsulfanyl]-N-methyl-N-Phenyl-acetamide (Compound 5-15) was prepared in similar fashion in 43% yield using N-methyl-N-phenyl chloroacetamide, m.p. 120–121° C.

2-[Bis-(4-fluoro-phenyl)-(2-fluoro-phenyl)-methylsulfanyl]-1-piperidin-1-yl-ethanone (Compound 5-16) was prepared in similar fashion in 42% yield using piperidinyl chloroacetamide, m.p. 128–129° C.

2-[Bis-(4-fluoro-phenyl)-(2-fluoro-phenyl)-methylsulfanyl]-acetamide (Compound 5-17) was prepared in similar fashion in 63% yield using iodoacetamide, THF as solvent and $K_2CO_3$ as base, m.p. 119–120° C.

2-[Bis-(4-fluoro-phenyl)-(2-fluoro-phenyl)-methylsulfanyl]-propionamide (Compound 5-18) was prepared in similar fashion in 28% yield using acrylamide, m.p. 133–134° C.

[Bis-(4-fluoro-phenyl)-(2-fluoro-phenyl)-methylsulfanyl]-acetonitrile (Compound 5-19)

A solution of chloroacetonitrile (5.45 mmol) was added dropwise to a stirring mixture of o-fluorophenyl-di-p-fluorophenylmethyl sulfide (4.54 mmol) and potassium carbonate (9.1 mmol) in THF (20 ml) at room temperature under Argon. After stirring for 2.5 hours at room temparature, 3.5 hours at 40° C. and 2 hours at 60° C. the mixture was poured into ice-cold water. Extraction with ethyl ether (3×), drying of the combined organic extracts ($Na_2SO_4$), filtration, concentration and flash-chromatography of the residue gave the title compound (41 %; M.p. 111–112° C.).

[(2-Fluoro-phenyl)-bis-(4-fluoro-phenyl)-methylsulfanyl]-acetic acid (Compound 5-20)

A solution of di-p-fluorophenyl-o-fluorophenylcarbinol (0.2 g) was dissolved in trifluoroacetic acid (3 ml) and treated with mercaptoacetic acid (0.5 ml) at room temperature. After stirring for 4 hours at room temperature the reaction was poured into water. Extraction with ethyl ether (3×), drying of the combined organic extracts ($Na_2SO_4$), filtration, concentration and flash-chromatography of the residue gave the title compound (69%; M.p. 112–113° C.).

2-[Bis-(4-fluoro-phenyl)-(2-fluoro-phenyl)-methylsulfanyl]-thioacetamide (Compound 5-21)

A solution of 2-[bis-(4-fluoro-phenyl)-(2-fluoro-phenyl)-methylsulfanyl]-acetamide (0.5 g) in toluene (20 ml) was treated with Lawesson's reagent (0.26 g) at room temperature under Argon and stirred for 1.5 hours at 80° C. After pouring into saturated brine the organics were extracted with dichloromethane (3×). Drying of the combined organic extracts ($Na_2SO_4$), filtration, concentration and flash-chromatography of the residue gave the title compound (42%; Isolated as an oil).

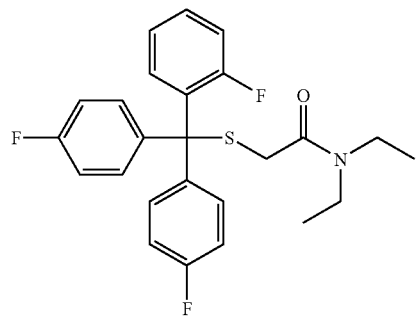

5-14

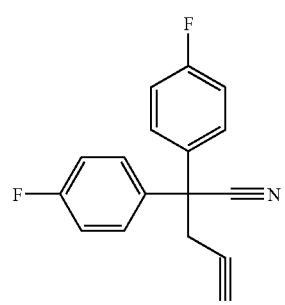

5-15

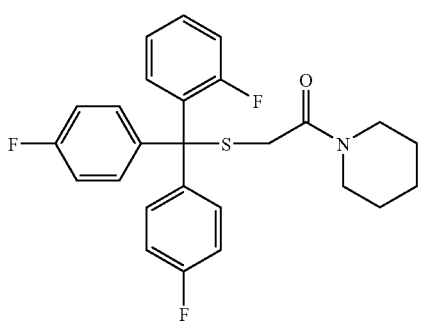

5-16

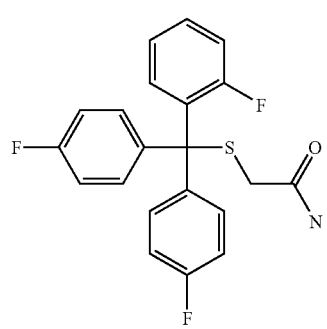

5-17

-continued

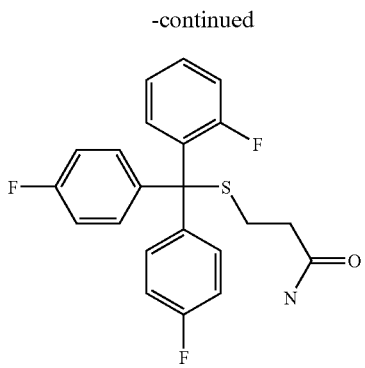
5-18

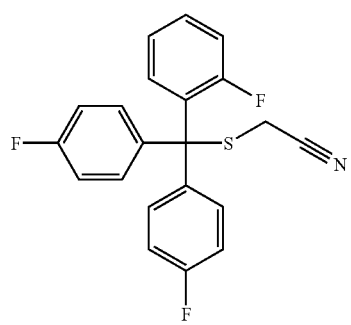
5-19

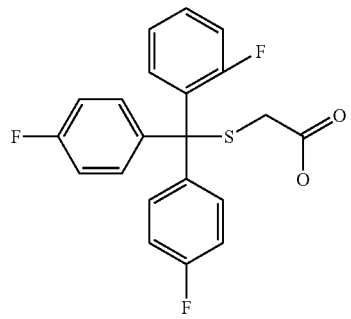
5-20

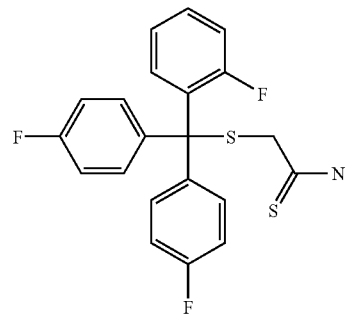
5-21

General Method for the Preparation of Compound Type 6
Synthesis of Tri Substituted Methyl Sulfoxide

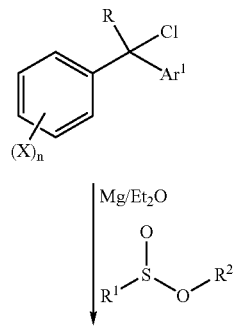

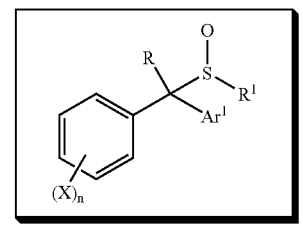

Compound Type-6

A compound Type 5 is dissolved in dichloromethane (DCM) (3 mL/mmol), cooled to −5° C., and 3-chloroperoxybenzoic acid (MCPBA) (1.0 equivalent) is added in small portions over 30 minutes. After 30 minutes at room temperature the reaction mixture is poured into water and extracted with DCM, dried with magnesium sulfate, filtrated and the solvent removed under reduced pressure. The crude product is purified by column chromatography (benzin:ethyl acetate) affording a compound Type 6 in 80–95% yield.

In this way the following tri substituted methyl sulfoxides are obtained:

Methyl tris(4-fluorophenyl)methyl sulfoxide (Compound 6-1);

Ethyl (bis(4-fluorophenyl)phenyl)methyl sulfoxide (Compound 6-2);

Cyclohexylmethyl tris(4-fluorophenyl)methyl sulfoxide (Compound 6-3);

Cyclohexyl tris(4-fluorophenyl)methyl sulfoxide (Compound 6-4);

Isopropyl tris(4-fluorophenyl)methyl sulfoxide (Compound 6-5);

(2-Thiazolyl)methyl tris(4-fluorophenyl)methyl sulfoxide (Compound 6-6);

Phenyl tris(4-fluorophenyl)methyl sulfoxide (Compound 6-7);

1-Methyl-2-imidazolyl tris(4-fluorophenyl)methyl) sulfoxide (Compound 6-8);

2-Pyridyl tris(4-fluorophenyl)methyl sulfoxide (Compound 6-9);

(Cyclohexyl-bis(4-fluorophenyl))methyl phenyl sulfoxide (Compound 6-10);

(Cyclopentyl-bis(4-fluorophenyl))methyl methyl sulfoxide (Compound 6-11); and (Cyclohexyl-(4-fluorophenyl)-(2-thiazolyl))methyl methyl sulfoxide (Compound 6-12).

6-1
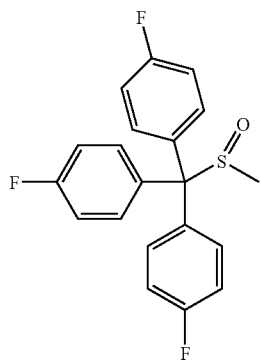
6-2
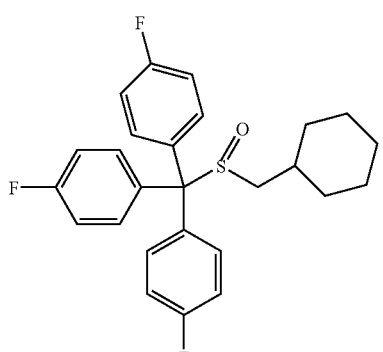
6-3
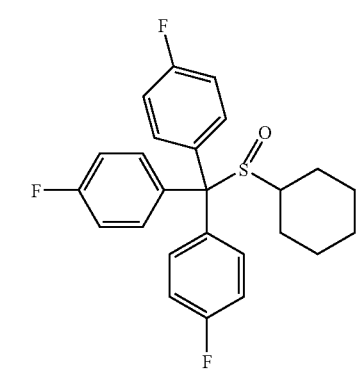
6-4
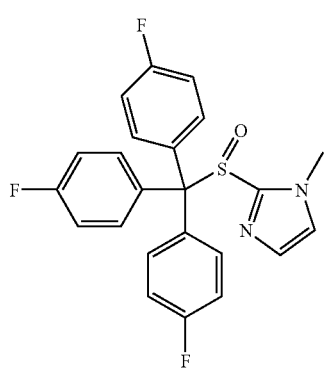
6-5
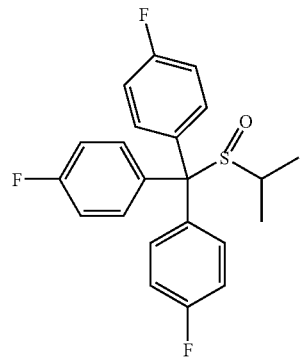
6-6
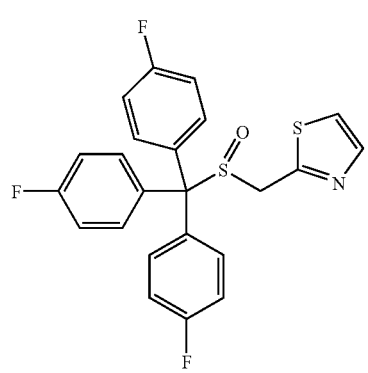
6-7
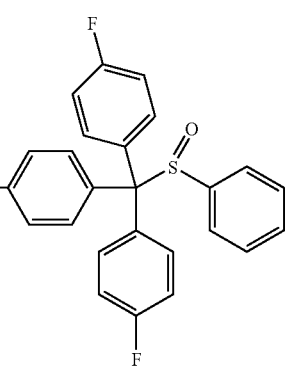
6-8

-continued

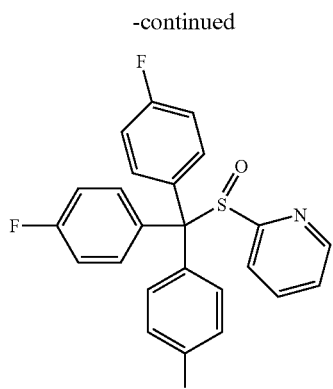
6-9

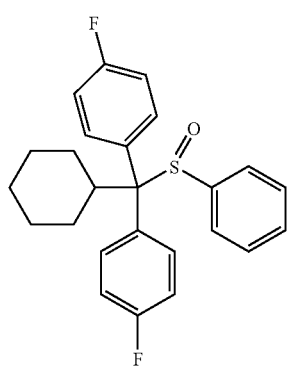
6-10

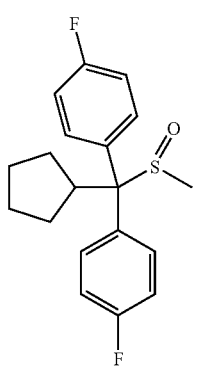
6-11

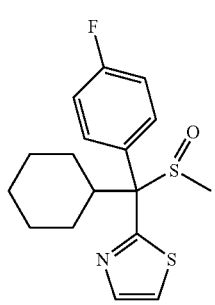
6-12

General Method for the Preparation of Compound Type 7
Synthesis of Sulfone

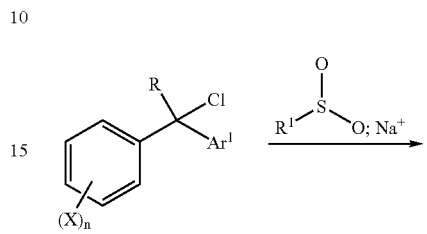

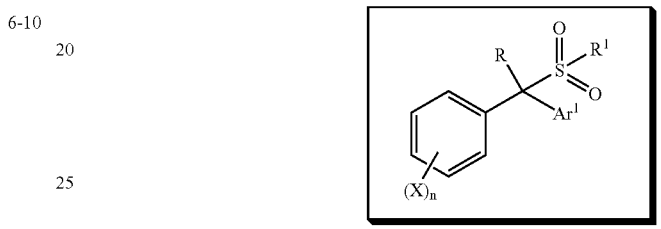

Compound Type-7

To a solution of a compound Type 2 and a sodium sulphinate (1.5 equivalent) in dimethyl sulfoxide (DMSO) (2 mL/mmol) is heated to 60° C. for 4 hours. The reaction mixture is poured into water, extracted with diethyl ether, dried with sodium sulfate, filtrated and the solvent removed under reduced pressure to give 80–88% yield. The crude product is purified by crystallization from acetic acid to give 45–55% yield.

In this way the following sulfones are obtained:

Methyl tris(4-fluorophenyl)methyl sulfone (Compound 7-1); Mp. 140.6–145.3° C.;

Ethyl (bis(4-fluorophenyl)phenyl)methyl sulfone (Compound 7-2);

Cyclohexylmethyl tris(4-fluorophenyl)methyl sulfone (Compound 7-3);

Cyclohexyl tris(4-fluorophenyl)methyl sulfone (Compound 7-4);

Isopropyl tris(4-fluorophenyl)methyl sulfone (Compound 7-5);

(2-Thiazolyl)methyl tris(4-fluorophenyl)methyl sulfone (Compound 7-6);

Phenyl tris(4-fluorophenyl)methyl sulfone (Compound 7-7); Mp. 157.4–160.6° C.;

1-Methyl-2-imidazolyl tris(4-fluorophenyl)methyl) sulfone (Compound 7-8);

2-Pyridyl tris(4-fluorophenyl)methyl sulfone (Compound 7-9);

(Cyclohexyl-bis(4-fluorophenyl))methyl phenyl sulfone (Compound 7-10);

(Cyclopentyl-bis(4-fluorophenyl))methyl methyl sulfone (Compound 7-11);

(Cyclohexyl-(4-fluorophenyl)-(2-thiazolyl))methyl methyl sulfone (Compound 7-12);

((2-Fluorophenyl)-bis(4-fluorophenyl)-phenyl)methyl methyl sulfone (Compound 7-13); and Methanesulphonyl-2-fluorophenyl-bis-(4-fluoro-phenyl) methane (Compound 7-14); (76%; M.p. 147–149° C.).

7-1
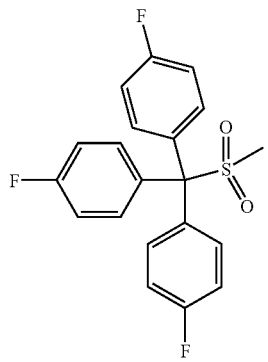
7-5
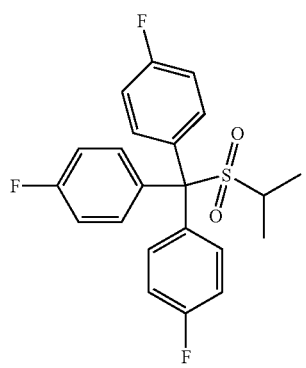
7-2
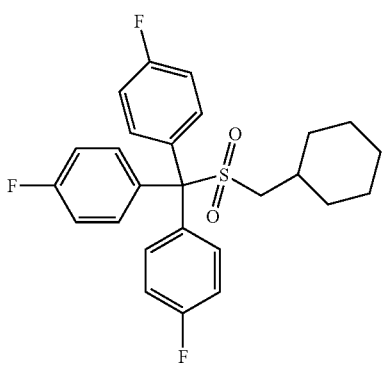
7-6
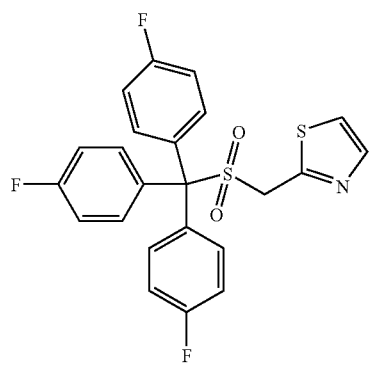
7-3
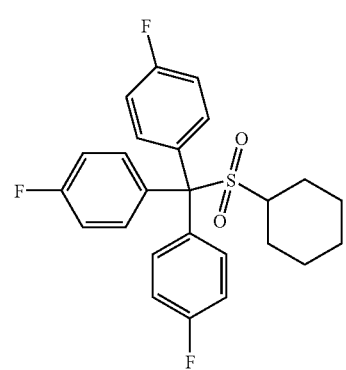
7-7
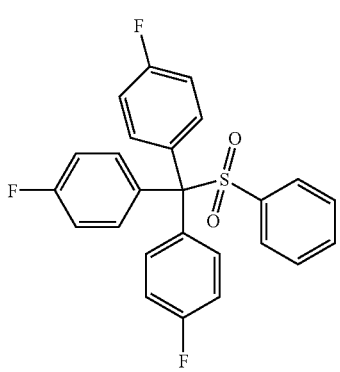
7-4
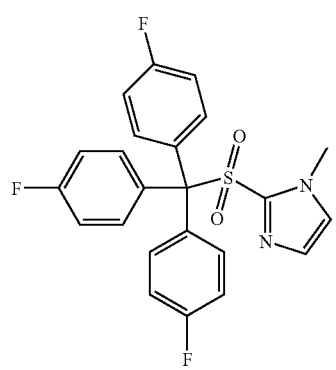

-continued
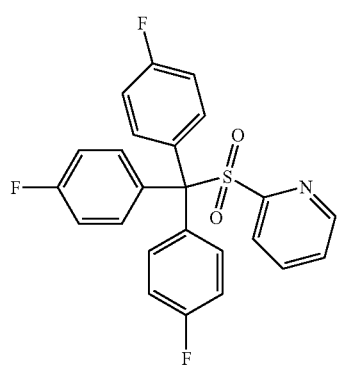
7-9
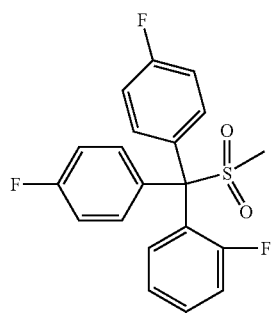
7-13
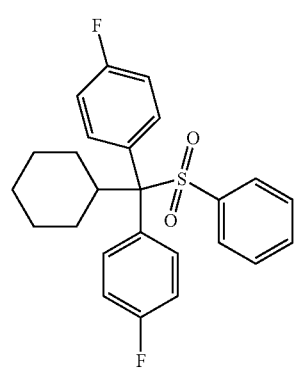
7-10
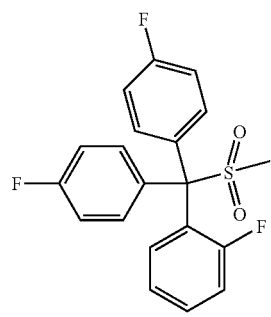
7-14
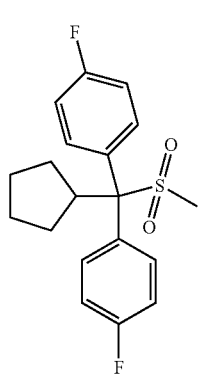
7-11
General Method for the Preparation of Compound Type 8
Synthesis of Sulfin Amides
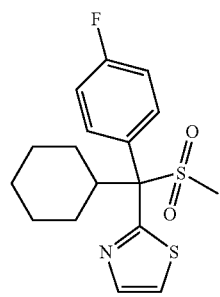
7-12
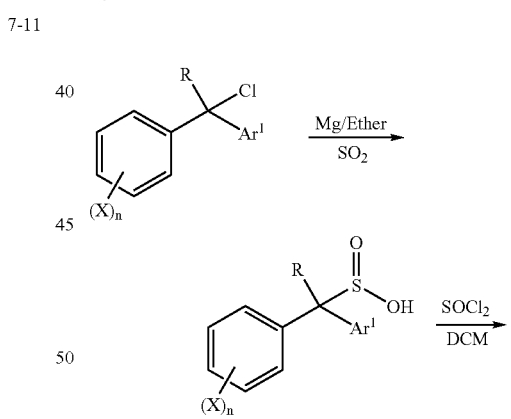
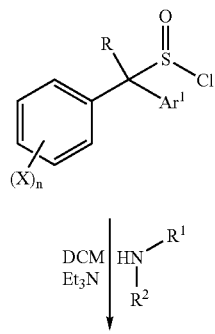

-continued

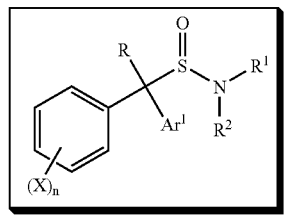

Compound Type-8

Magnesium tunings in anhydrous diethyl ether is heated to gentle reflux, and a solution of compound Type 2 (1 equivalent) in anhydrous diethyl ether is added slowly from a dropping funnel at such a rate that gentle reflux continue without further heating. When the addition is completed, the reaction mixture is heated to gentle reflux until only traces of unreacted magnesium remains. This Grignard reagent is used in the next step.

Anhydrous diethyl ether in a 3-neck flask is cooled in an acetone/$CO_2$ bath. The flask is fitted with a $SO_2$ inlet adaptor, a dropping funnel with the Grignard reagent and an outlet gas trap with aq. NaOH.

$SO_2$ is condensed, in the cooled ether, by a gentle flux through the outlet gas trap. The Grignard reagent is added drop wise from the funnel during 1 hour.

The sulfinic acid is liberated by acidic work-up and is dissolved in dichloromethane (10ml/g). Thionyl chloride (1 equivalent) is added and the mixture is heated to reflux until the evolution of gasses ceases. The reaction mixture is cooled in an ice bath and a solution of the appropriate amine (2 equivalents) in dichloromethane is added. The resulting mixture is stirred at ambient or elevated temperature until completion of the reaction.

In this way the following sulfin amides are obtained:

Tris-(4-fluorophenyl)-methanesulfinic acid amide (Compound 8-1);
Bis-(4-fluorophenyl)-phenyl-methanesulfinic acid methylamide (Compound 8-2);
Tris-(4-fluorophenyl)-methanesulfinic acid cyclohexylamide (Compound 8-3);
1-[Tris-(4-fluorophenyl)-methanesulfinyl]-piperidine (Compound 8-4);
Tris-(4-fluorophenyl)-methanesulfinic acid dimethylamide (Compound 8-5);
Tris-(4-fluorophenyl)-methanesulfinic acid thiazol-2-ylamide (Compound 8-6);
Tris-(4-fluorophenyl)-methanesulfinic acid (4-fluorophenyl)-amide (Compound 8-7);
Bis-(4-fluorophenyl)-(1-methyl-1H-imidazol-2-yl)-methanesulfinic acid methylamide (Compound 8-8);
Cyclohexyl-(4-fluorophenyl)-thiazol-2-yl-methanesulfinic acid amide (Compound 8-9);
Bis-(4-fluorophenyl)-(1-methyl-1H-imidazol-2-yl)-methanesulfinic acid amide (Compound 8-10);
Bis-(4-fluorophenyl)-thiazol-2-yl-methanesulfinic acid amide (Compound 8-11); and
Bis-(4-fluorophenyl)-oxazol-2-yl-methanesulfinic acid amide (Compound 8-12).

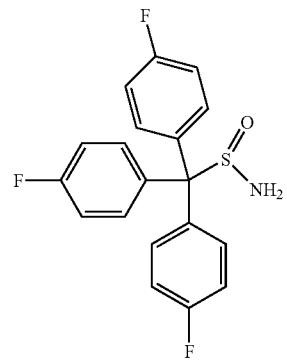

8-1

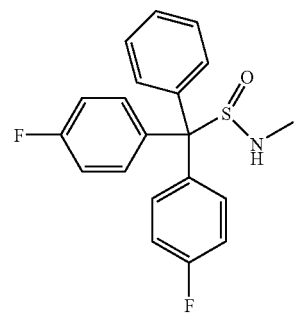

8-2

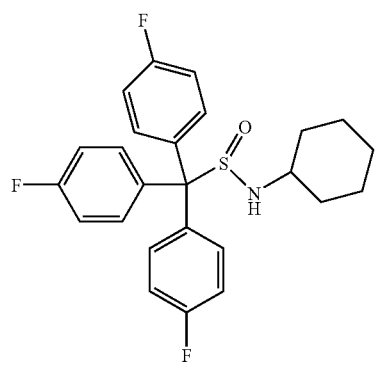

8-3

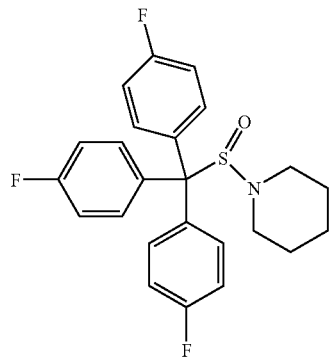

8-4

-continued
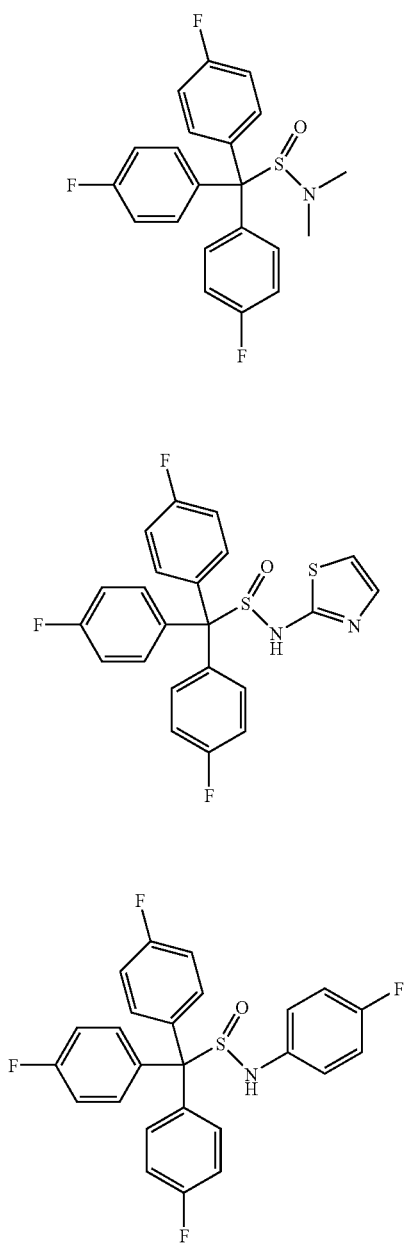
-continued
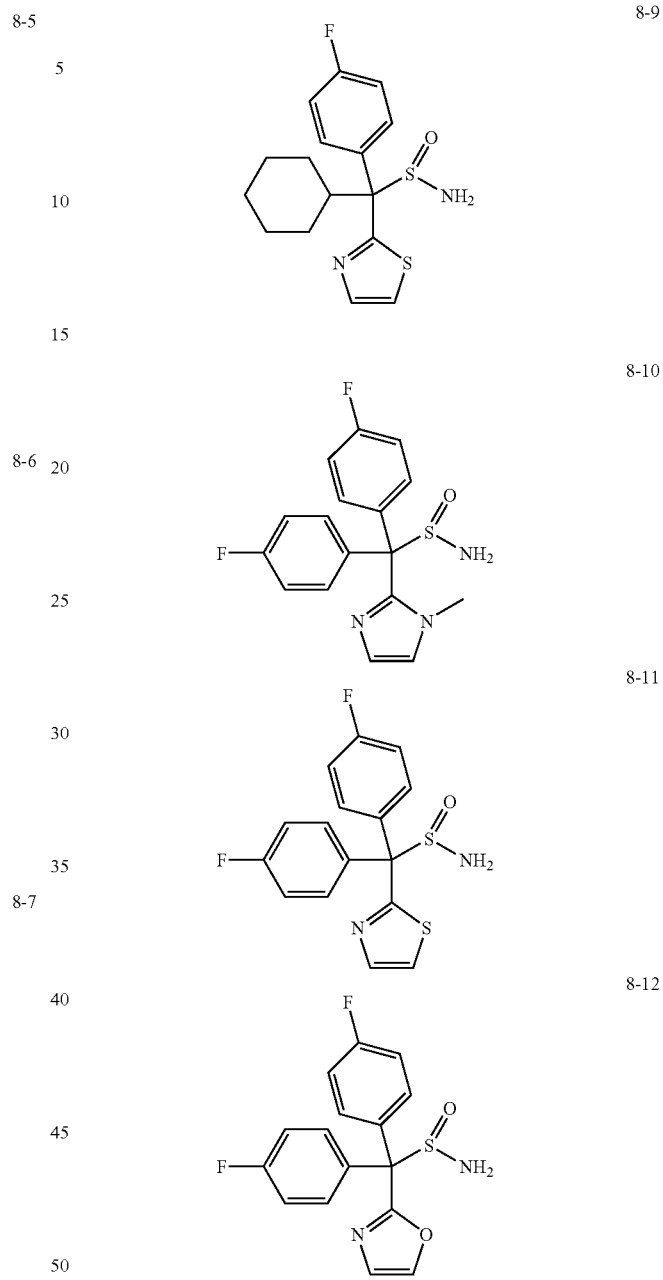
General Method for the Preparation of Compound Type 9
Synthesis of Thiocarbamate
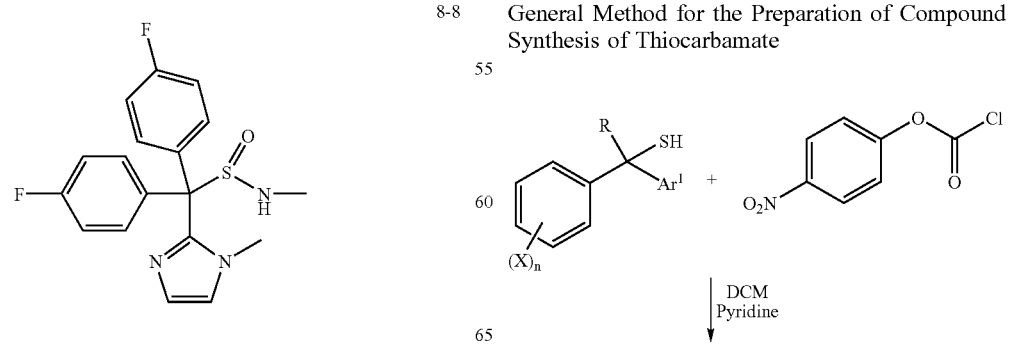

-continued

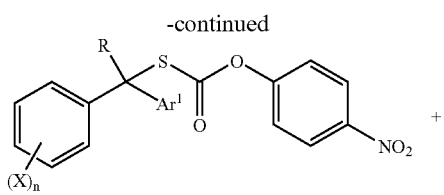

Thiocarbamic acid S-[cyclohexyl-(4-fluorophenyl)-pyridin-2-yl-methyl] ester (Compound 9-9);

Dimethyl-thiocarbamic acid S-[tris-(4-fluorophenyl)-methyl]ester (Compound 9-10);

Thiocarbamic acid S-[(2-fluorophenyl)-bis-(4-fluorophenyl)-methyl]ester (Compound 9-11); and Thiocarbamic acid S-[(2-fluorophenyl)-(4-fluorophenyl)-phenyl-methyl]ester (Compound 9-12).

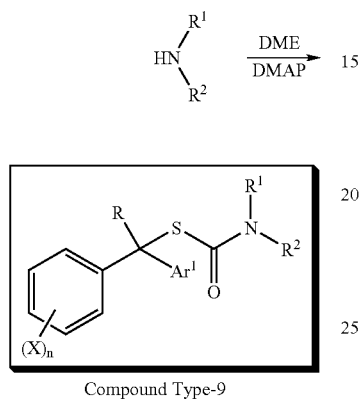

Compound Type-9

A compound Type 3 is dissolved in dichloromethane (DCM) (3 mL/mmol), pyridine (1 equivalent) and 4-nitrophenyl chloroformate (1 equivalent) are added and the solution is heated to refluxed for 3 hour. The reaction mixture is cooled washed with aq hydrochloric acid, 10% sodium carbonate and water. Dried with magnesium sulfate, filtrated and the solvent removed under reduced pressure. The crude product is purified by column chromatography affording substituted thiocarbonate.

The substituted thiocarbonate is dissolved in dimethoxyethane (DME) (3 mL/mmol), and the amine is added (1 equivalent) together with 4-dimethylaminopyridine (DMAP) (1 equivalent). The reaction mixture is heated for 14 hours at 50° C., cooled to room temperature, washed with aq hydrochloric acid, 10% sodium carbonate and water. Dried with magnesium sulfate, filtrated and the solvent removed under reduced pressure. The crude product is purified by column chromatography affording substituted thiocarbamate.

In this way the following thiocarbamates are obtained:

Thiocarbamic acid S-[tris-(4-fluorophenyl)-methyl]ester (Compound 9-1);

Thiocarbamic acid S-[cyclohexyl-bis-(4-fluorophenyl)-methyl]ester(Compound 9-2);

Thiocarbamic acid S-[cyclohexyl-(4-fluorophenyl)-thiazol-2-yl-methyl]ester (Compound 9-3);

Piperidine-1-carbothioic acid S-[tris-(4-fluorophenyl)-methyl]ester (Compound 9-4);

Methyl-thiocarbamic acid S-[cyclopentyl-bis-(4-fluorophenyl)-methyl]ester (Compound 9-5);

Pyrrolidine-1-carbothioic acid S-[cyclohexyl-bis-(4-fluorophenyl)-methyl]ester (Compound 9-6);

Methyl-thiocarbamic acid S-[tris-(4-fluorophenyl)-methyl]ester (Compound 9-7);

Methyl-thiocarbamic acid S-[cyclopentyl-(2-fluorophenyl)-(4-fluorophenyl)-methyl]ester (Compound 9-8);

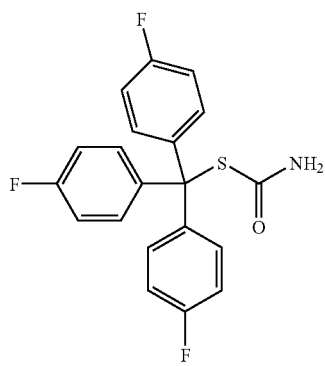

9-1

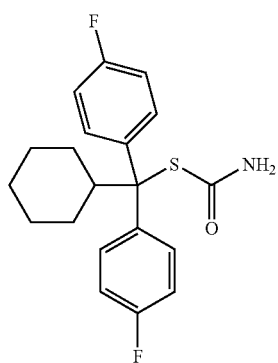

9-2

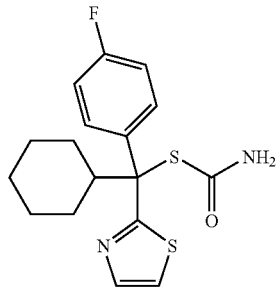

9-3

-continued
9-4
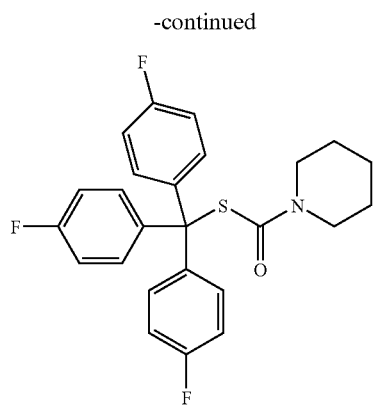
9-5
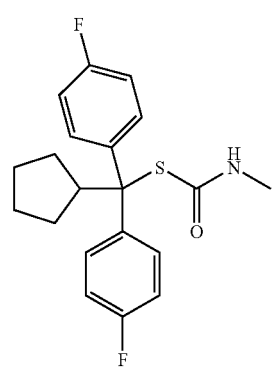
9-6
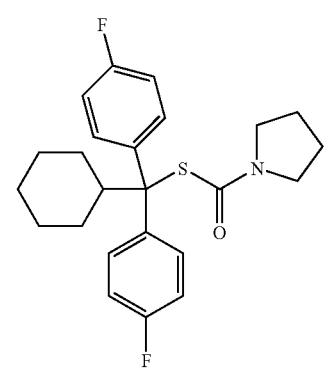
9-7
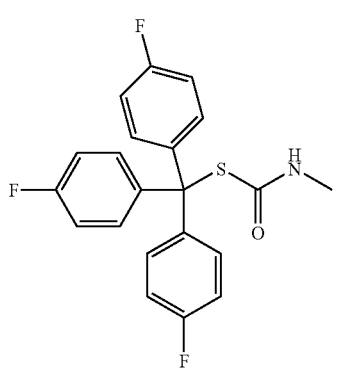
-continued
9-8
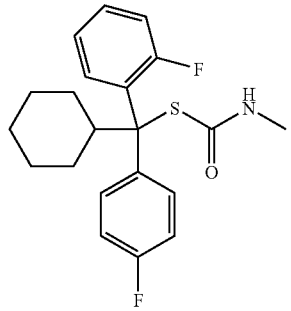
9-9
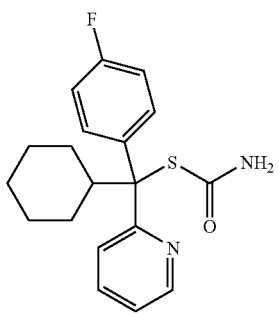
9-10
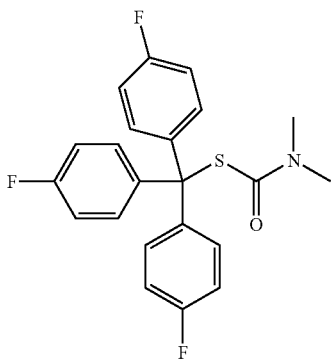
9-11
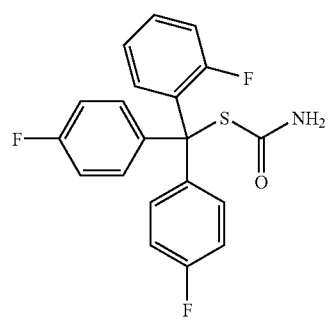
9-12
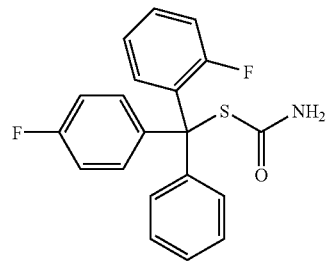

General Method for the Preparation of Compound Type 10
Synthesis of Phosphonate

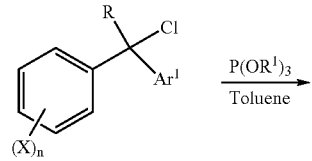

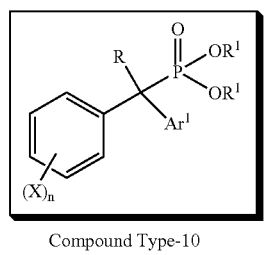

Compound Type-10

A compound Type 2 in toluene (2 mL/mmol) and trialkyl phosphite (4 equivalent) is heated at reflux for 16 hours under a nitrogen atmosphere. The reaction mixture is cooled and the volatiles are removed under reduced pressure. The crude product is purified by column chromatography (benzin:ethyl acetate) (20:1) or by crystallization from benzin, affording alkyl phosphonate in 61-82% yield.

In this way the following phosphonates are obtained:

[Tris-(4-fluorophenyl)-methyl]-phosphonic acid dimethyl ester (Compound 10-1); Mp. 131.6° C.;

[(2-Fluorophenyl)-bis-(4-fluorophenyl)-methyl]-phosphonic acid dimethyl ester (Compound 10-2); Mp. 136.6° C.;

[(3-Fluorophenyl)-bis-(4-fluorophenyl)-methyl]-phosphonic acid dimethyl ester (Compound 10-3);

2-[Tris-(4-fluorophenyl)-methyl]-[1,3,2]dioxaphospholane 2-oxide (Compound 10-4);

[Cyclohexyl-bis-(4-fluorophenyl)-methyl]-phosphonic acid dimethyl ester (Compound 10-5);

Cyclopentyl-bis-(4-fluorophenyl)-methyl]-phosphonic acid dipropyl ester (Compound 10-6);

[(4-Chlorophenyl)-bis-(4-fluorophenyl)-methyl]-phosphonic acid dimethyl ester (Compound 10-7);

[1,1-Bis-(4-fluorophenyl)-hexyl]-phosphonic acid dimethyl ester (Compound 10-8);

[1,1-Bis-(4-fluorophenyl)-2-methyl-propyl]-phosphonic acid dimethyl ester (Compound 10-9);

[Bis-(4-fluorophenyl)-pyridin-2-yl-methyl]-phosphonic acid dimethyl ester (Compound 10-10); and

[Bis-(4-fluorophenyl)-thiazol-2-yl-methyl]-phosphonic acid dimethyl ester (Compound 10-11).

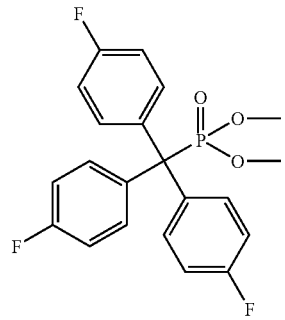

10-1

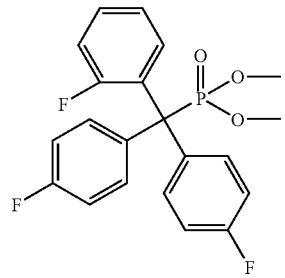

10-2

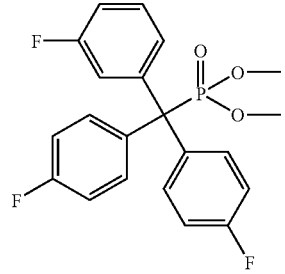

10-3

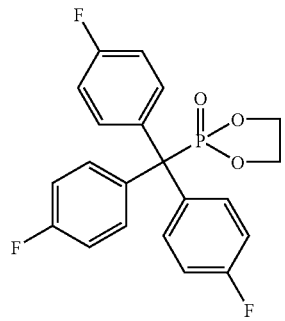

10-4

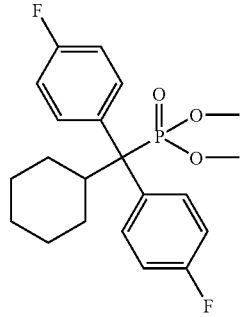

10-5

-continued 10-6

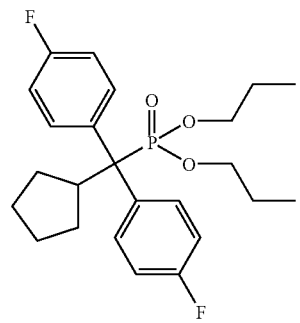

10-7

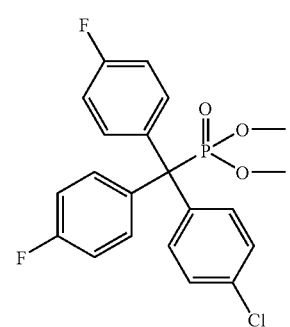

10-8

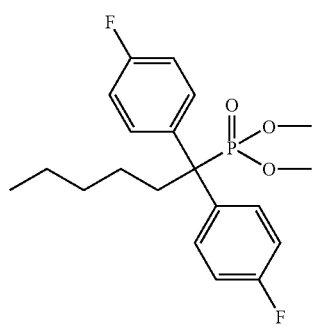

10-9

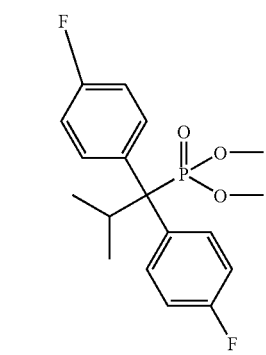

10-10

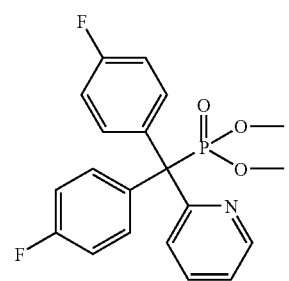

-continued 10-11

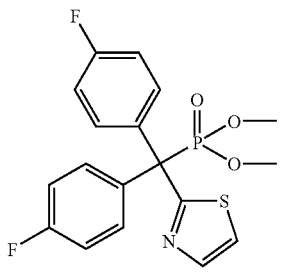

[(2-Chloro-phenyl)-(2-fluoro-phenyl)-(4-fluoro-phenyl)-methyl]-phosphonic acid di-methyl ester (Compound 10-12)

Chloro tri-p-fluorophenylmethane (860 mg) dissolved in toluene (15 ml) was treated with trimethylphosphite (449 mg) and the reaction was refluxed for 6 hours. Toluene was evaporated and the crude residue purified by flash chromatography to afford 62% of the dimethyl phosphonate ester of the title compound (97%; M.p. 131,5-1 32,5° C.).

[(4-Chloro-phenyl)-bis-(4-fluoro-phenyl)-methyl]-phosphonic acid dimethyl ester (Compound 10-13)

Chloro tri-p-fluorophenylmethane (860 mg) dissolved in toluene (15 ml) was treated with trimethylphosphite (449 mg) and the reaction was refluxed for 6 hours. Toluene was evaporated and the crude residue purified by flash chromatography to afford 62% of the dimethyl phosphonate ester of the title compound (67%; M.p. 136-137° C.).

[Bis-(4-fluoro-phenyl)-(2-fluoro-phenyl)-methyl]-phosphonic acid (Compound 10-14)

To a solution of the phosphonate [(2-Fluoro-phenyl)-bis-(4-fluoro-phenyl)-methyl]-phosphonic acid dimethyl ester (195 mg) in acetonitrile (7 ml) was added iodotrimethylsilane (0.17 ml) under Argon. The reaction mixture was left stirring for 3 hrs and then the volatiles were evaporated. 10 ml each of water and chloroform were added to the residue and the mixture was stirred for a further 30 min. The organic phase was separated and the water layer was extracted twice more with CHCl$_3$. Drying of the combined organic extracts with MgSO$_4$, filtration, concentration and recrystallisation of the residue from acetonitrile afforded a white solid (100 mg; M.p. 228-230° C.).

[Bis-(4-fluoro-phenyl)-p-tolyl-methyl]-phosphonic acid (Compound 10-15) was prepared in similar fashion in 72% yield, m.p. 240° C. (decomposes).

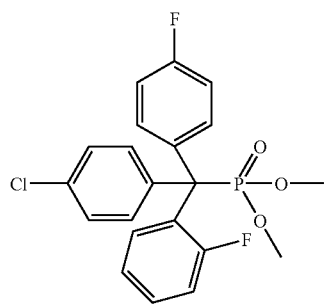

10-12

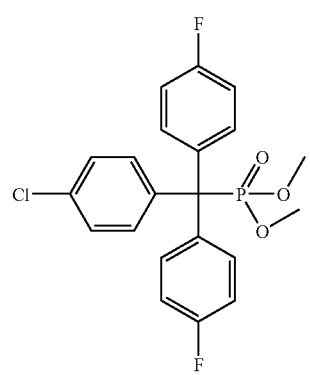

10-13

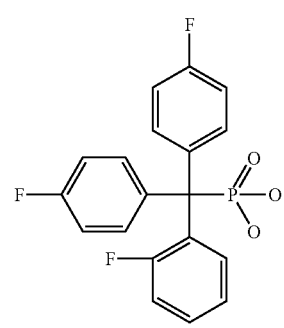

10-14

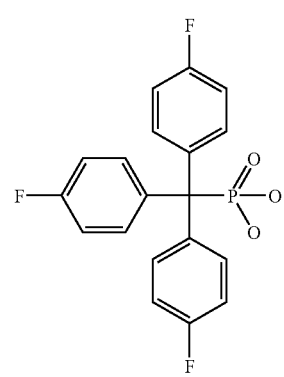

10-15

General Method for the Preparation of Compound Type 11
Synthesis of Phosphonate

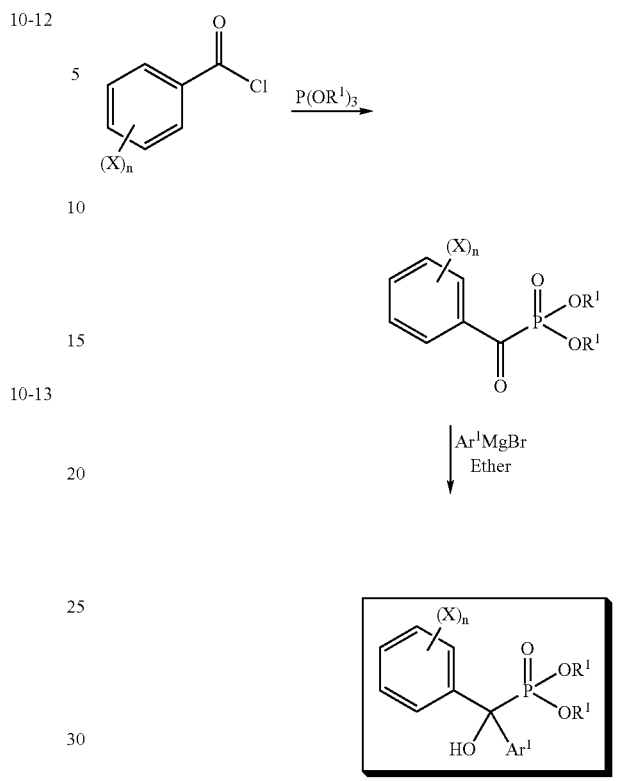

Compound Type-11

A substituted benzoyl chloride is cooled to 10° C. and trialkyl phosphite (1.1 equivalent) is added slowly from a dropping funnel during 2 hours, with vigorous stirring under nitrogen. An exothermic reaction with evolution of alkyl chloride gas takes place, and the reaction temperature is maintained below 30° C. (ice/water bath). The reaction is completed at room temperature for 3–5 hours with a gentle flux of nitrogen, and then distilled at reduced pressure ($10^{-2}$ Torr) to give substituted dialkyl benzoylphosphonates in 69–95% yield.

The substituted dialkyl benzoylphosphonates prepared as described above is added to a fresh prepared Grignard reagent (1.1 equivalent) in ether at −78° C. After 15 minutes the reaction mixture is poured into 0.1 M HCl, extracted with diethyl ether, dried with sodium sulfate, filtrated and the solvent removed under reduced pressure to give crude product. The crude product is purified by column chromatography (benzin:ethyl acetate) or by crystallization from benzin, affording Type 11 compound in 45–60% yield.

General Method for the Preparation of Compound Type 12
Synthesis of Phosphonate

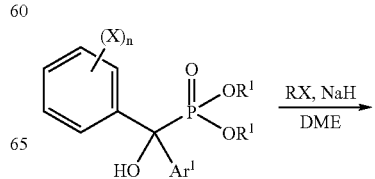

-continued

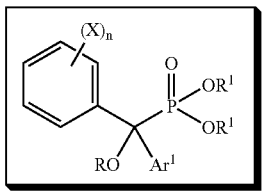

Compound Type-12

A compound of Type 11 is deprotonated by treatment with sodium hydride (1 equivalent) in dichloromethane. The resulting alcoholate ion is alkylated by treatment with the appropriate alkyl halide under standard conditions.

In this way the following phosphonates are obtained:
[Bis-(4-fluorophenyl)-isopropoxy-methyl]-phosphonic acid dimethyl ester (Compound 12-1);
[(2-Fluorophenyl)-(4-fluorophenyl)-isobutoxy-methyl]-phosphonic acid dimethyl ester (Compound 12-2); and
2-[Bis-(4-fluorophenyl)-isopropoxy-methyl]-[1,3,2]-dioxaphospholane 2-oxide (Compound 12-3).

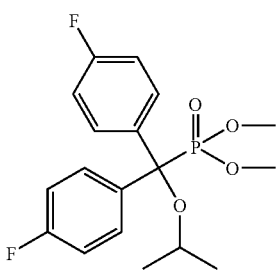

12-1

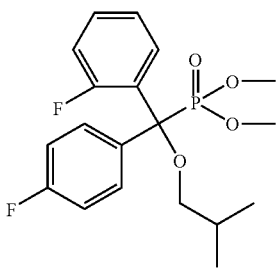

12-2

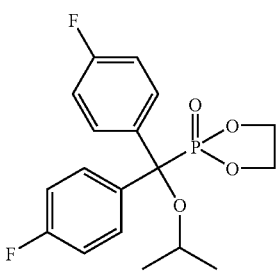

12-3

The invention claimed is:

1. A compound according to Formula I

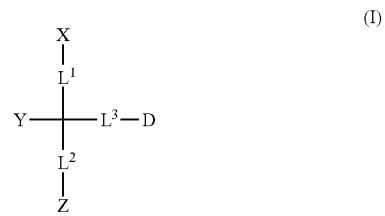

or any of its enantiomers or any mixture of its enantiomers, or a pharmaceutically acceptable salt thereof, wherein
  $L^1$, $L^2$, and $L^3$ are absent;
  X and Y both represent a phenyl group, which phenyl group is substituted with halogen;
  Z represents alkyl, alkenyl, alkynyl, or cycloalkyl; and
  D represents —CN, $R^6$—CN, or —CON($R^2R^3$), wherein $R^2$ and $R^3$, independently of each another, represent hydrogen or alkyl; and
  $R^6$ represents alkyl.

2. The compound of claim 1, which is
  2-(2-Fluoro-phenyl)-2-(4-fluoro-phenyl)-pent-4-enenitrile;
  2-(2-Fluoro-phenyl)-2-(4-fluoro-phenyl)-3-methyl-butyronitrile;
  2,2-Bis-(4-fluoro-phenyl)-3-methyl-butyronitrile;
  2,2-Bis-(4-fluoro-phenyl)-4-methyl-pentanenitrile;
  2,2-Bis-(4-fluoro-phenyl)-pent-4-enenitrile;
  2,2-Bis-(4-fluoro-phenyl)-pent-4-ynenitrile;
  2-(2-Fluoro-phenyl)-2-(4-fluoro-phenyl)-pent-4-ynenitrile;
  2-(2-Fluoro-phenyl)-2-(4-fluoro-phenyl)-4-methyl-pentanenitrile;
  2-(3-Fluoro-phenyl)-2-(4-fluoro-phenyl)-3-methyl-butyronitrile;
  2-(3-Fluoro-phenyl)-2-(4-fluoro-phenyl)-4-methyl-pentanenitrile;
  2-(3-Fluoro-phenyl)-2-(4-fluoro-phenyl)-pent-4-enenitrile;
  2-(3-Fluoro-phenyl)-2-(4-fluoro-phenyl)-pent-4-ynenitrile; or
  2,2-Bis-(4-fluoro-phenyl)-3-methyl-butyramide;
  or any of its enantiomers or any mixture of its enantiomers, or a pharmaceutically acceptable salt thereof.

3. A pharmaceutical composition comprising a therapeutically effective amount of a compound of claim 1, or a pharmaceutically-acceptable addition salt thereof, together with at least one pharmaceutically-acceptable carrier or diluent.

4. The compound of claim 1, wherein X and Y both represent a phenyl group substituted with fluoro or chloro.

5. The compound of claim 1, wherein X and Y both represent a phenyl group substituted with fluoro.

6. The compound of claim 1, wherein Z represents alkyl.

7. The compound of claim 1, wherein D represents —CN.

8. The compound of claim 1, wherein D represents —CON($R^2R^3$), wherein $R^2$ and $R^3$, independently of each another, represent hydrogen or alkyl.

9. The compound of claim 1, wherein D represents —CON($R^2R^3$), wherein $R^2$ and $R^3$ hydrogen.

10. The compound of claim 1, which is 2,2-Bis-(4-fluorophenyl)-3-methyl-butyronitrile, or a pharmaceutically acceptable salt thereof.

11. The compound of claim 1, which is 2,2-Bis-(4-fluorophenyl)-3-methyl-butyramide, or a pharmaceutically acceptable salt thereof.

* * * * *